(12) United States Patent
Berner et al.

(10) Patent No.: US 8,592,481 B2
(45) Date of Patent: *Nov. 26, 2013

(54) GASTRIC RETENTIVE GABAPENTIN DOSAGE FORMS AND METHODS FOR USING SAME

(71) Applicant: Depomed, Inc., Newark, CA (US)

(72) Inventors: Bret Berner, Half Moon Bay, CA (US); Sui Yuen Eddie Hou, Foster City, CA (US); Theophilus J. Gana, Leesburg, VA (US); Marilou S. Cramer, Redwood City, CA (US)

(73) Assignee: Depomed, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/707,961

(22) Filed: Dec. 7, 2012

(65) Prior Publication Data
US 2013/0116320 A1 May 9, 2013

Related U.S. Application Data

(63) Continuation of application No. 12/331,184, filed on Dec. 9, 2008, which is a continuation of application No. 11/648,134, filed on Dec. 29, 2006, now abandoned, which is a continuation-in-part of application No. 11/322,448, filed on Dec. 29, 2005.

(51) Int. Cl.
*A61K 31/195* (2006.01)
*A61K 9/22* (2006.01)
*A61K 9/52* (2006.01)

(52) U.S. Cl.
USPC .......................... 514/561; 424/457; 424/468

(58) Field of Classification Search
None
See application file for complete search history.

(56) References Cited

U.S. PATENT DOCUMENTS

| | | |
|---|---|---|
| 3,574,820 A | 4/1971 | Johnson et al. |
| 3,845,770 A | 11/1974 | Theeuwes et al. |
| 3,977,404 A | 8/1976 | Theeuwes |
| 4,024,175 A | 5/1977 | Satzinger et al. |
| 4,087,544 A | 5/1978 | Satzinger et al. |
| 4,152,326 A | 5/1979 | Hartenstein et al. |
| 4,309,406 A | 1/1982 | Guley et al. |
| 4,404,183 A | 9/1983 | Kawata et al. |
| 4,462,839 A | 7/1984 | McGinley et al. |

(Continued)

FOREIGN PATENT DOCUMENTS

| | | |
|---|---|---|
| CA | 2220038 | 7/1999 |
| CA | 2143500 | 4/2007 |

(Continued)

OTHER PUBLICATIONS

U.S. Appl. No. 09/425,491, Shell et al.

(Continued)

*Primary Examiner* — Kortney L Klinkel
(74) *Attorney, Agent, or Firm* — McDermott Will & Emery LLP

(57) ABSTRACT

Provided is a method of treating a patient suffering from a pain state by administering to the patient a gastric retentive dosage form of gabapentin that is capable of administration in once-daily or twice daily dosing regimens. By reducing the need to administer gabapentin from the thrice-daily administrations characteristic of immediate release gabapentin, the gastric retentive gabapentin dosage forms provided herein have the advantages of improving patient compliance for gabapentin treatment. In addition to the foregoing, the gastric retentive gabapentin dosages forms also exhibit decreased blood plasma concentrations and increased bioavailability throughout the dosing regimen.

12 Claims, 5 Drawing Sheets

(56) References Cited

U.S. PATENT DOCUMENTS

| | | |
|---|---|---|
| 4,612,008 A | 9/1986 | Wong et al. |
| 4,753,801 A | 6/1988 | Oren et al. |
| 4,828,836 A | 5/1989 | Elger et al. |
| 4,851,232 A | 7/1989 | Urquhart et al. |
| 4,871,548 A | 10/1989 | Edgren et al. |
| 4,894,476 A | 1/1990 | Butler et al. |
| 4,996,058 A | 2/1991 | Sinnreich |
| 5,007,790 A | 4/1991 | Shell |
| 5,084,479 A | 1/1992 | Woodruff et al. |
| 5,232,704 A | 8/1993 | Franz et al. |
| 5,273,758 A | 12/1993 | Royce |
| 5,382,435 A | 1/1995 | Geary et al. |
| 5,443,843 A | 8/1995 | Curatolo et al. |
| 5,558,879 A | 9/1996 | Chen et al. |
| 5,582,837 A | 12/1996 | Shell |
| 5,591,452 A | 1/1997 | Miller et al. |
| 5,660,861 A | 8/1997 | Jao et al. |
| 5,783,212 A | 7/1998 | Fassihi et al. |
| 5,872,984 A | 2/1999 | Berglund et al. |
| 5,906,832 A | 5/1999 | Jao et al. |
| 5,945,125 A | 8/1999 | Kim |
| 5,955,103 A | 9/1999 | Jao et al. |
| 5,972,389 A | 10/1999 | Shell et al. |
| 6,024,977 A | 2/2000 | Yatvin et al. |
| 6,024,982 A | 2/2000 | Oshlack et al. |
| 6,054,482 A | 4/2000 | Augart et al. |
| 6,068,859 A | 5/2000 | Curatolo et al. |
| 6,117,453 A | 9/2000 | Seth et al. |
| 6,120,803 A | 9/2000 | Wong et al. |
| 6,162,466 A | 12/2000 | Licht et al. |
| 6,187,338 B1 | 2/2001 | Caruso et al. |
| 6,242,488 B1 | 6/2001 | Bueno et al. |
| 6,255,526 B1 | 7/2001 | Pesachovich et al. |
| 6,273,340 B1 | 8/2001 | Rivailler et al. |
| 6,294,192 B1 | 9/2001 | Patel et al. |
| 6,294,198 B1 | 9/2001 | Vilkov |
| 6,294,690 B1 | 9/2001 | Deering et al. |
| 6,310,098 B1 | 10/2001 | Guttuso, Jr. |
| 6,333,352 B1 | 12/2001 | Derakshan |
| 6,340,475 B2 | 1/2002 | Shell et al. |
| 6,346,270 B1 | 2/2002 | Shivanand et al. |
| 6,350,471 B1 | 2/2002 | Seth |
| 6,451,808 B1 | 9/2002 | Cowles |
| 6,465,012 B2 | 10/2002 | Vilkov |
| 6,488,962 B1 | 12/2002 | Berner et al. |
| 6,488,964 B2 | 12/2002 | Bruna et al. |
| 6,635,280 B2 | 10/2003 | Shell et al. |
| 6,635,281 B2 | 10/2003 | Wong et al. |
| 6,682,759 B2 | 1/2004 | Lim et al. |
| 6,683,112 B2 | 1/2004 | Chen et al. |
| 6,723,340 B2 | 4/2004 | Gusler et al. |
| 7,438,927 B2 | 10/2008 | Berner et al. |
| 7,612,112 B2 | 11/2009 | Berner et al. |
| 7,731,989 B2 | 6/2010 | Berner et al. |
| 8,119,166 B2 | 2/2012 | Berner et al. |
| 8,192,756 B2 | 6/2012 | Berner et al. |
| 2001/0004644 A1 | 6/2001 | Levine |
| 2001/0008889 A1 | 7/2001 | Caruso et al. |
| 2001/0036943 A1 | 11/2001 | Coe et al. |
| 2001/0043946 A1 | 11/2001 | Vilkov |
| 2001/0046473 A1 | 11/2001 | Besse |
| 2001/0055607 A1 | 12/2001 | Levine |
| 2002/0012679 A1 | 1/2002 | Bruna et al. |
| 2002/0012680 A1 | 1/2002 | Patel et al. |
| 2002/0082252 A1 | 6/2002 | Hochman |
| 2002/0107208 A1 | 8/2002 | Chen et al. |
| 2002/0115705 A1 | 8/2002 | Magnus-Miller et al. |
| 2002/0142050 A1 | 10/2002 | Straub et al. |
| 2003/0031711 A1 | 2/2003 | Fara et al. |
| 2003/0044466 A1 | 3/2003 | Markey et al. |
| 2003/0064036 A1 | 4/2003 | Petereit et al. |
| 2003/0091630 A1 | 5/2003 | Louie-Helm et al. |
| 2003/0100611 A1 | 5/2003 | Berner et al. |
| 2003/0104052 A1 | 6/2003 | Berner et al. |
| 2003/0104053 A1 | 6/2003 | Gusler et al. |
| 2003/0104062 A1 | 6/2003 | Berner et al. |
| 2003/0133985 A1 | 7/2003 | Louie-Helm et al. |
| 2003/0152622 A1 | 8/2003 | Louie-Helm et al. |
| 2003/0181390 A1 | 9/2003 | Gallop et al. |
| 2004/0053853 A1 | 3/2004 | Almarsson et al. |
| 2004/0062802 A1 | 4/2004 | Hermelin |
| 2004/0180088 A1 | 9/2004 | Dudhara et al. |
| 2004/0185105 A1 | 9/2004 | Berner et al. |
| 2005/0064036 A1 | 3/2005 | Berner et al. |
| 2005/0158380 A1 | 7/2005 | Chawia et al. |
| 2005/0169982 A1 | 8/2005 | Almarssoo et al. |
| 2006/0094785 A1 | 5/2006 | Guttuso, Jr. |
| 2006/0159743 A1 | 7/2006 | Berner et al. |
| 2006/0167032 A1 | 7/2006 | Galer et al. |
| 2006/0264509 A1 | 11/2006 | Fraser et al. |
| 2007/0184104 A1 | 8/2007 | Berner et al. |
| 2008/0161393 A1 | 7/2008 | Barrett et al. |
| 2008/0226715 A1 | 9/2008 | Cha et al. |
| 2008/0299204 A1 | 12/2008 | Nangia et al. |
| 2009/0017121 A1 | 1/2009 | Berner et al. |
| 2009/0137565 A1 | 5/2009 | Frucht |
| 2009/0175939 A1 | 7/2009 | Bosse et al. |
| 2009/0176882 A1 | 7/2009 | Berner et al. |
| 2010/0063148 A1 | 3/2010 | Christoph et al. |
| 2010/0190752 A1 | 7/2010 | Schiene et al. |
| 2010/0226981 A1 | 9/2010 | Karaborni et al. |
| 2010/0247610 A1 | 9/2010 | Berner et al. |
| 2010/0297229 A1 | 11/2010 | Sesha |
| 2011/0053914 A1 | 3/2011 | Schiene et al. |
| 2011/0207718 A1 | 8/2011 | Bird |
| 2011/0218246 A1 | 9/2011 | Berner et al. |
| 2011/0268666 A1 | 11/2011 | Friedman et al. |
| 2012/0027823 A1 | 2/2012 | Berner et al. |
| 2012/0064129 A1 | 3/2012 | Berner et al. |
| 2012/0064168 A1 | 3/2012 | Berner et al. |
| 2012/0128735 A1 | 5/2012 | Berner et al. |

FOREIGN PATENT DOCUMENTS

| | | |
|---|---|---|
| DE | 4432757 A1 | 3/1996 |
| EP | 0458751 A1 | 5/1991 |
| EP | 1118321 | 7/2001 |
| WO | WO 90/11757 A1 | 10/1990 |
| WO | WO 92/04013 A1 | 3/1992 |
| WO | WO 93/18755 A1 | 9/1993 |
| WO | WO 95/29665 A1 | 11/1995 |
| WO | WO 96/26718 A2 | 9/1996 |
| WO | WO 96/32097 A1 | 10/1996 |
| WO | WO 97/18814 A1 | 5/1997 |
| WO | WO 97/47285 A1 | 12/1997 |
| WO | WO 98/11879 A1 | 3/1998 |
| WO | WO 98/55107 A1 | 12/1998 |
| WO | WO 98/56360 A1 | 12/1998 |
| WO | WO 99/12537 A1 | 3/1999 |
| WO | WO 99/47128 A1 | 9/1999 |
| WO | WO 00/53225 A1 | 9/2000 |
| WO | WO 00/59477 A1 | 10/2000 |
| WO | WO 00/76478 A1 | 12/2000 |
| WO | WO 01/13894 A1 | 3/2001 |
| WO | WO 01/37812 A1 | 5/2001 |
| WO | WO 01/56544 A2 | 8/2001 |
| WO | WO 01/97612 A1 | 12/2001 |
| WO | WO 01/97782 A1 | 12/2001 |
| WO | WO 03/002101 A1 | 1/2003 |
| WO | WO 03/002151 A1 | 1/2003 |
| WO | WO 03/011255 A1 | 2/2003 |
| WO | WO 03/035040 A1 | 5/2003 |

OTHER PUBLICATIONS

U.S. Appl. No. 10/045,816, filed Oct. 25, 2001, Berner et al.

Adelman and Adelman, "Current options for the prevention and treatment of migrane", Clin. Ther., vol. 23, No. 6, pp. 772-788 (2001).

Adler, "Treatment of restless legs syndrome with gabapentin", Clin. Neuropharmacol., vol. 20, No. 2, pp. 148-151 (1997).

Andrews et al., "Gabapentin: a new agent for the management of epilepsy", Ann. Pharmacother., vol. 28, pp. 1188-1196 (1994).

(56) References Cited

OTHER PUBLICATIONS

Apicella et al., "Poly(ethylene oxide) (PEO) and different molecular weight PEO blends monolithic devices for drug release", Biomaterials, vol. 14, No. 2, pp. 83-90 (1993).
Asconape et al., "Myclonus associated with the use of gabapentin", Epilepsia, vol. 41, pp. 479-481(2000).
Ashton et al., "GABA-ergic drugs exit stage left, enter stage right", Journal of Psychopharmacology, vol. 17, No. 2, pp. 174-178 (2003).
Babu et al., "In vitro and vivo studies of sustained-release floating dosage forms containing salbutamol sulfate", Pharmazie, vol. 45, pp. 268-270 (1990).
Backonja et al., "Gabapentin for the symptomatic treatment of painful neuropathy in patients with diabetes milletus", JAMA, vol. 280, pp. 1831-1836 (1998).
Bazil and Bazil, "Recent advances in the pharmacotherapy of epilepsy", Clin. Ther., vol. 19, Issue 3, pp. 369-382 (1997).
Bebin et al., "New anticonvulsant drugs, focus on flunarizine, fosphenytoin, midazolam and stripentol", Drugs, vol. 48, pp. 153-171 (1994).
Benedetti, "Enzyme induction and inhibition by new antiepileptic drugs: a review of human studies", Fund. Clin. Pharmac., vol. 14, pp. 301-319 (2000).
Benetello et al., "Oral gabapentin disposition in patients with epilepsy after a high-protein meal", Epilepsia, vol. 38, No. 10, pp. 1140-1142 (1997).
Ben-Menachem, "New antiepileptic drugs and non-pharmacological treatments", Curr. Opin. Neurol., vol. 13, pp. 165-170 (2000).
Bennett et al., "Gabapentin in the treatment of neurophathic pain", Palliative Med., vol. 18, No. 1, pp. 5-11 (2004).
Bennett et al., "Future directions in the management of pain by intraspinal drug delivery", J. Pain and Symptom Management, vol. 20, No. 2, pp. S44-S50 (2000).
Bernus et al., "Anticonvulsant therapy in aged patients: clinical pharmacokinetic considerations", Drugs & Aging, vol. 10, pp. 278-289 (1997).
Beydoun et al., "Gabapentin: pharmacokinetics, efficacy, and safety", Clinical Neuropharmacoloqy, vol. 18, No. 6, pp. 469-481 (1995).
Beydoun, "Monotherapy trial of new antiepileptic drugs", Epilepsia, vol. 38, No. 9, pp. S21-S31 (1997).
Bialer, "Comparative pharmacokinetios of the newer antiepilieptic drugs", Clin. Pharmacokinet., vol. 24, pp. 441-452 (1993).
Blum et al., "Pharmacokinetics of gabapentin in subject with various degrees of renal function", Clin. Pharmacol. Ther., vol. 56, pp. 154-159 (1994).
Bolger et al., "Simulation of the nonlinear dose dependence for substrates of influx and efflux transporters in the human intestine", The AAPS Journal, vol. 11, No. 2, pp. 353-363 (2009).
Bourgeois, "Important pharmacokinetic properties of antiepileptic drugs", Epilepsia, vol. 36, pp. 5, pp. S1-S7 (1995).
Bourgeois, "New antiepileptic drugs", Arch. Neurol., vol. 55, pp. 1184-1183 (1998).
Bourgeois, "Pharmacokinetic properties of current antiepileptic drugs: what improvements are needed?", Neurology, vol. 55, No. 3, pp, S11-S16 (2000).
Boyd et al., "Clinical research: effects of age and gender on single-dose pharmacokinetics of gabapentin" Epilepsia, vol. 40, pp. 474-479 (1999).
Brown et al., "Cloning and deletion mutagenesis of the $\alpha_2\delta$ calcium channel subunit from porcine cerebral cortex", J. Biol. Chem., vol. 273, pp. 25458-25465 (1998).
Browne, "Long-term efficacy and toxicity of gabapentin", Neurology, vol. 43, pp. A307 (1993).
Bryans et al., "3-substitute GABA analogs with central nervous system activity: A review", Medicinal Research Reviews, vol. 19, No. 2, pp. 149-177 (1999).
Chadwick et al., "Clinical administration of new antiepileptic drugs, an overview of safety and efficacy", Epilepsia, vol. 37, No. 6, pp. S17-S22 (1996).
Chadwick, "An overview of the efficacy and tolerability of new antiepileptic drugs", Epilepsia, vol. 38, No. 1, pp. S59-S62 (1997).
Chadwick, "Gabapentin", Lancet, vol. 343, pp. 89-91 (1994).
Collins et al., "Extended release formulations medications", CNS Drugs, vol. 14, No. 3, pp. 203-212 (2000).
Cramer et al., "New antiepileptic drugs: comparison of key clinical trials", Epilepsia, vol. 40, pp. 590-600 (1999).
Curry et al., "Newer antiepileptic drugs: gabapentin, felbamate, topirimate and fosphenytoin", Am. Family Physcian, vol. 57, pp. 513-520 (1998).
Davis et al., "Relationship between the rate of appearance of oxyprenolol in the systematic circulation and the location of an oxyprenolol oros 16/260 drug delivery system within the gastrointestinal tract as determined by scintigraphy", Br. J. Clin. Pharmac., vol. 26, pp. 435-443 (1988).
Davis et al., "Transit of pharmaceutical dosage forms through the small intestine", Gut, vol. 27, pp. 886-892 (1986).
Davis et al., "The effect of density on the gastric emptying of single- and multiple-unit dosage forms", Pharmaceutical Research, vol. 3, No. 4, pp. 208-213 (1986).
Deshpande et al., "Development of a novel controlled-release system for gastric retention" Pharm. Res., vol. 14, No. 6, pp. 815-819 (1997).
Devinsky et al., "New antiepileptic drugs for children: felbamate, gabapentin, lamotrigine and vigabatrin", J. Child Neurology, vol. 9, No. 1, pp. S33-S45 (1994).
Di Trapani et al., "Gabapentin in the prophylaxis of migrane: a double-blind randomized placebo-controlled study", Clin. Ter., vol. 151, No. 3, pp. 145-148 (2000) Abstract only.
Dow Chemical U.S.A. Product Information Publication, "Formulating for controlled release with methocel cellulose ethers", Oct. 5, 2007, pp. 1-34.
"Drug delivery to the gastrointestinal tract", Hardy et al., ed , *Ellis Horwood books in biological sciences, Series in pharrnaceutical technology*, Ellis Horwood Limited, Halsted Press: a division of John Wiley & Sons, New York, NY, USA, Chapter 3, pp. 37-48, (1989).
Dworkin et al., "Advances in neuropathic pain: diagnosis, mechanisms, and treatment recommendations", Archives of Neurology, vol. 60, pp. 1524-1534 (2003).
Eckhardt et al., "Gabapentin enhances the analgesic effect of morphine in healthy volunteers", Anesth. Analges., vol. 91, pp. 185-191 (2000).
Edgren et al., "Controlled release technology, pharmaceutical", *Kirk-Othmer encyclopedia of Chemical Technology*, John Wiley & Sons, Inc., Online ISBN: 9780471238966, DOI: 10.1002/0471238961, 24 pgs. (2000).
Eldon et al., "Lack of effect of gabapentin on the pharmacokinetics of a norethindrone acetate/ethinyl estradiol-containing oral contraceptive", Neurology, vol. 43, pp. A307 (1993).
Elger et al., "New antiepileptic drugs in eliptology", Neuropsychobiol., vol. 38, pp. 145-148 (1998).
Elwes et al., "Clinical pharmacokinetics of newer antiptileptic drugs", Clin. Pharmcokinet., vol. 30, pp. 403-415 (1996).
Emilien et al., "Pharmacological managetment of epilepsy, mechanism of action, pharmacokinetics drug interactions, and new drug discovery possibilities", Intl. J. Clin. Pharmacol. Ther., vol. 36, pp. 181-194 (1998).
Fara, "Physiological Limitations: Gastric Emptying and Transit of Dosage Forms", *Rate Control in Drug Therapy*, L.F. Prescott, et al., eds., Churchill Livingstone, New York, (1985).
Feely and Davis, "Correlation of phenylpropanolamine bioavailability with gastrointestinal transit by scintigraphic monitoring of 111In-labeled hydroxypropylmethylcellulose matrices", Pharmaceutical Research, vol. 6, No. 4, pp. 274-278 (1989).
Feely, "Fortnightly review: drug treatment of epilepsy", BMJ, vol. 318, pp. 106-109 (1999).
Ferrier, "Lamotrigine and gabapentin: alternatives in the treatment of bipolar disorder", Neuropsychobiol , vol. 38, pp. 192-197 (1998).
Fischer et al., "Lack of serious toxicity following gabapentin overdose", Neurology, vol. 44, pp. 982-983 (1994).
Fix, "Oral drug delivery, Small intestine and colon", *Controlled Delivery*, Mathiowitz, Ed., Wiley & Sons, Inc., pp. 699-700 (1999).

(56) References Cited

OTHER PUBLICATIONS

Ford et al., "Importance of drug type, tablet shape and added diluents on drug release kinetics from hydroxypropylmethylcellulose matrix tablets", Int'l. J. Pharmaceutics, vol. 40, pp. 223-234 (1987).
Freeman et al., "Mood stabilizer combinations: a review of safety and efficacy", Am. J. Psychiatry, vol. 155, pp. 12-21 (1998).
Fromm, "Gabapentin: discussion", Epilepsia, vol. 25, No. 5, pp. S77-S90 (1994).
Genton, "When antiepileptic drugs aggravate epilepsy," Brain Dev., vol. 22, pp. 75-80 (2000).
Ghaemi et al., "Gabapentin treatment of the non-refractory bipolar spectrum: an open case series," J. Affective Disorders, vol. 65. pp. 167-171 (2001).
Gidal et al., "Gabapentin absorption: effect of mixing with foods of varying macronutrient composition", Ann. Pharmacother., vol. 32, pp. 405-409 (1998).
Gidal et al., "Gabapentin bioavailability: effect of dose and frequency of administration in adult patients wlth epilepsy", Epilepsy Research, vol. 31, No. 2, pp. 91-99 (1998).
Goa et al., "Gabapentin: a review of its pharmacological properties and clinical potential in epilepsy", Drugs, vol. 46, No. 3, pp. 409-427 (1993).
Gram, "Pharmacokinetics of new antiepileptic drugs", Epilepsia, vol. 37, No. 6, pp. S12-S16 (1996).
Grundy and Foster, "The nifedipine Gastrointestinal Therapeutic System (GITS), Evaluation of Pharmaceutical, Pharmacokinetic and Pharmacological Properties", Clin. Pharmacokinet., vol. 26, pp. 435-443 (1988).
Guberman, "Monotherapy or polytherapy for epilepsy", Canadian J. Neurol. Sci., vol. 25, pp. S3-S8 (1998).
Gusler et al., "Pharmacokinetics of metformin gastric-retentive tablets in healthy volunteers", J. Clin. Pharmacol., vol. 41. No. 6, pp. 655-661 (2001).
Guttuso, Jr. et al., "Gabapentins effects on hot flashes in postmenopausal women: a randomized controlled trial", Am. College of Obstetricians and Gynecologists, vol. 101, No. 2, pp. 337-345 (2003).
Handforth, "Efficacy and tolerance of long-term, high-dose gabapentin: additional observations", Epilepsia, vol. 25, pp. 1032-1037 (1994).
Hansen, "Treatment of chronic pain with antiepileptic drugs: a new era", Southern Med. J., vol. 92, pp. 642-649 (1999).
Hou et al., "Gastric retentive dosage forms: a review", Crit. Rev. Ther. Drug Carrier Syst., vol. 20, No. 6, pp. 461-497 (2003).
Hunt et al., "A relation between the chain length of fatty acids and the slowing of gastric emptying", J. Physiol., vol. 194, pp. 327-336 (1968).
Hwang, "Gastric retentive drug-delivery systems", Critical Reviews in Therapeutic Drug Carrier Systems, vol. 15, No. 3, pp. 243-284 (1998).
Irving et al., "Efficacy and safety of extended-release gabapentin for the treatment of postherpetic neuralgia", Abstract and poster presented at the 9$^{th}$ Int. Conf. on the Mechanisms and Treatment of Neuropathic Pain (2006).
Johnston, "GABA agonists as targets for drug development", Clin. Exp. Pharmacol. Physiol., vol. 19, pp. 73-78 (1992).
Kalviainen et al., "A double-blind study of gabapentin in treatment of partial seizures", Epilepsia, vol. 30, pp. 661 (1989).
Kelly, "Gabapentin—antiepileptic mechanism of action", Neuropsychology, vol. 38, pp. 139-144 (1998).
Khosla and Davis, "The effect of tablet size on the gastric emptying of non-disintergrating tablets", Int. J. Pharm., vol. 82, pp. R9-R11 (1990).
Khurana et al., "Efficacy of gabapentin therapy in children with refractory partial seizures", J. Pediatrics. vol. 128, pp. 829-833 (1996).
Kim, "Drug release from compressed hydrophilic POLYOX-WSR tablets", J. Pharmaceutical Sci., vol. 84, No. 3, pp. 303-306 (1995).
Kriel et al., "Failure of absorption of gabapentin after rectal administration", Epilepsia, vol. 38, No. 1, pp. 1242-1244 (1997) Abstract only.
Kushnir et al., "Analysis of gabapentin in serum and plasma by solid-phase extraction and gas chromatography-mass spectrometry for therapeutic drug monitoring", J. Anal. Toxicol., vol. 23, pp. 1-6 (1999).
Laird et al., "Use of gabapentin in the treatment of neuropathic pain", Ann. Pharmacotherapy, vol. 34, pp. 802-807 (2000).
Lal et al., "Clinical pharmacokinetic drug interaction studies of gabapentin enacarbil, novel transported prodrug of gabapentin, with naproxen and cimetidine", Br. J. Clin. Pharmacol., vol. 69, No, 5., pp. 498-507 (2010).
Lee et al., "Oral mucosa controlled delivery of LHRH by bilayer mucoadhesive polymer systems" J. Contr. Rel., vol. 19, pp. 251-261 (1995).
Leiderman et al., "Gabapentin as add-on therapy for refractory partial epilepsy: results of five placebo-controlled trials", Epilepsia, vol. 35, No. 5, pp. S74-S76 (1994).
Leppik, "Antiepileptic drugs in development: prospects for the near future", Epilepsia, vol. 35, Suppl. 4, pp. S29-S40 (1994).
Letterman et al., "Gabapentin: a review of published experience in the treatment of bi-polar disorder and other psychiatric conditions", Pharmacother., vol. 19, pp. 565-572 (1999).
Loiseau, "Treatment of concomitant illnesses in patients receiving anticonvulsants: drug interactions of clinical significance", Drug Safety, vol. 19, pp. 495-510 (1998).
MacDonald et al., "Antiepileptic drug mechanisms of action", Epilepsia, vol. 34, No. 5, pp. S1-S8 (1993).
Magnus, "Nonepileptic uses of gabapentin", Epilepsia, vol. 40, No. 6, pp. S6-S72 (1999).
Mancardi et al., "Gapapentin is effective in treating nocturnal painful tonic spasms in multiple sclerosis", Neurology, vol. 52, No. 2, pp. A134 (1999).
Mao et al., "Gabapentin in pain management", Anaesth. Analges., vol. 91, pp. 680-687 (2000).
Mathew et al., "Efficacy of gabapentin in migraine prophylaxis", Headache, vol. 41, pp. 119-128 (2001).
Mattson, "Antiepileptic drug monitoring: a reappraisal", Epilepsia, vol. 36, No. 5, pp. S22-S29 1995).
Maurer et al., "Intestinal absorption of gabapentin in rats", Arnzeim-Forsch/Drug Res., vol. 41, pp. 104-106 (1991).
McLean, "Gabapentin", Epilepsia, vol. 36. No. 2, pp. S73-S86 (1995).
McLean, "Gabapentin: chemistry, absorption, distribution, and excretion", *Antiepileptic Drugs*, 4$^{th}$ Edition, Levy, Mattson, and Meldrum, eds., Raven Press, Ltd., New York, NY, USA, pp. 843-849 (1995).
Meldrum, "Update on the mechanism of action of antiepileptic drugs", Epilepsia, vol. 37. Bo. 6, pp. S4-S11 (1996).
Miles et al., "Differentiating possible transport mechanisms for the intestinal absorption of gababentin", Pharmac. Res., vol. 11, No. 1, pp. S365 (1994).
Miles et al., "Variables affecting the intestinal absorption of water soluble and insoluble antiepileptic agents", Pharmac. Res., vol. 10, No. 10, pp. S223 (1993).
Morrell, "The new antiepileptic drugs and women: fertility, reproductive health, pregnancy and fetal outcome", Epilepsia, vol. 37, No. 6, pp. S34-S44 (1996).
Morrell, "Epilepsy in women: the science of why it is special", Neurology, vol. 53, No. 1, pp. S42-S48 (1999).
Morris, "Gabapentin", Epilepsia, vol. 40, No. 5, pp. S63-S70 (1999).
Muscas et al., "Conversion From Thrice Daily to Twice Daily Administration of Gabapentin (GBP) in Partial Epilepsy: Analysis of Clinical Efficacy and Plasma Levels", Seizure, vol. 9, No. 1, pp. 47-50 (2000).
NDA 20-235 (U.S. Food and Drug Administration application No. 020235), retrieved Dec. 22, 1993.
NDA 20-235 obtained via Freedom of Information Act, "Basics Pharmacokinetics Bioavailability"—optimal absorption, dose proportionality, and sustained release formulation (study #877-076) and "general comments to the medical reviewer.", retrieved Dec. 22, 1993.

(56) References Cited

OTHER PUBLICATIONS

NDA 20-882 (U.S. Food and Drug Administration application No. 020882), retrieved Nov. 18, 2010.
NDA 21-129 (U.S. Food and Drug Administration application No. 021129), retrieved Nov. 18, 2010.
Pande et al., "Placebo-controlled study of gabapentin treatment of panic disorder," J. Clin. Psychopharmacol., vol. 20, pp. 467-471 (2000).
Pande et al., "Treatment of social phobia with gabapentin: a placebo-controlled study", J. Clin. Psychopharmacol., vol. 19, pp. 341-348 (1999).
Pandya et al., "Gabapentin for hot flashes in 420 women with breast cancer: a randomized double-blind placebo-controlled trial", The Lancet, vol. 366, No. 9488, pp. 818-824 (2005).
Papadimitriou et al., "Swelling studies on mixtures of two hydrophilic excipients", S.T.P. Pharma Sciences. vol. 3, No. 3, pp. 232-236 (1993).
Park "Enzyme-digestible swelling hydrogels swelling hydrogels as platforms for long-term oral drug delivery: synthesis and characterization", Biomaterials, vol. 9, No. 5, pp. 435-441 (1988).
Parks et al., "Practical therapeutics: drug therapy for epilepsy", Am. Family Physican, vol. 50, pp. 639-648 (1994).
Patsalos et al., "Newer Antiepileptic drugs: towards an improved risk-benefit ratio," Drug Safety, vol. 11, pp. 37-67 (1994).
Perucca et al., "Antiepileptic drugs as a cause of worsening seizures", Epilepsia, vol. 39, pp. 5-17 (1998).
Perucca, "The new generation of antiepileptic drugs: advantages and disadvantages", Br. J. Clin. Psychcopharmacol., vol. 42, pp. 531-543 (1996).
"Pharmaceutical Dosage Forms" *Durgin and Hanan's Pharmacy Practice for Technicians*, 4th Edition, Durgin and Hanan, eds., Delmar Cengage Learning, Clifton Park, NY, USA, Chapter 12, pp. 198-228 (2008).
Piyapolrungroj et al., "Mucosal uptake of gabapentin (neurontin) vs. pregabalin in the small intestine", Pharm. Res., vol. 18, No. 8, pp. 1126-1130 (2001).
*POLYVOX: Water-Soluble Resins NF in Pharmaceutical Applications*, "An introduction to POLYVOX water soluble resins", The Dow Chemical Company, Brochure, 12 pgs (2004).
Raby, "Gabapentin therapy for cocaine cravings", Am. J Psychiatry, vol. 157, pp. 2058-2059 (2000).
Ragucci et al., "Gabapentin-induced hypersensitivity syndrome", Clin. Neuropharmacol., vol. 24, pp. 103-105 (2001).
Rao et al., "Influence of molecular size and water solubility of the solute on its release from swelling and erosion controlled polymeric matrices", J. Conrolled Release, vol. 12, Issue 2, pp. 133-141 (1990).
Remington: *The science and practice of pharmacy*, 19th Edition, Gennaro, ed., Mack Publishing Company, Easton, Pennsylvania, USA, Chapter 92, pp. 1628-1629 (1995).
Richter et al., "Pregabalin or morphine and gabapentin for neuropathic pain", Expert Op. on Pharmacotherapy, vol. 6, No. 14, pp. 2535-2539 (2005).
Riva et al., "Pharmacokinetics interactions between antiepileptic drugs: clinical considerations", Clin. Pharmacokinetics, vol. 31, pp. 470-493 (1996).
Rocci et al., "Food-induced gastric retention and absorption of sustained-release procainamide", Clin. Pharmacol. Ther., vol. 42, pp. 45-49 (1987).
Rosenberg et al., "The effect of gabapentin on neuropathic pain", Clin. J. Pain, vol. 13, pp. 251-255 (1997).
Rowan et al., "Intensive monitoring and pharmacokinetics studies of gabapentin in patients with generalized spike-wave discharges", Epilepsia, vol. 30, pp. 661 (1989).
Rowbotham et al., "Gabapentin for the treatment of postherpetic neuralgia, A randomized control study", JAMA, vol. 280, No. 21, pp. 1837-1842 (1998).
Sabers et al., "New anticonvulsants: comparative review of drug interactions and adverse effects", Drugs, vol. 60, pp. 23-33 (2000).
Salinsky et al., "Effects of chronic gabapentin and carbamazepine treatment on EEG, alertness and cognition in healthy volunteers", Epilepsia, vol. 41, No. 7, pp. 151, Abst. #2240 (2000).
Schmidt et al., "The new anticonvulsant drugs: implications for avoidance of adverse effects", Drug Safety, vol. 11, pp. 422-431 (1994).
Shalaby et al., "In vitro and in vivo studies of enzyme-digestible hydrogels for oral drug delivery", J. Controlled Release, vol. 19, pp. 131-144 (1992).
Shojaei and Berner, "Gastric retentive dosage forms", *Design of Controlled Release Drug Delivery Systems*, Li and Jasti, ed., McGraw Hill, New York, NY, USA, pp. 173-201 (2006).
Shovron et al., "Overview of the safety of newer antiepileptic drugs", Epilepsia, vol. 38, No. 1, pp. S45-S51 (1997).
Sindrup et al., "Efficacy of pharmacological treatments of neuropathic pain: an update and effect reiateci to mechanism of drug action", Pain, vol. 83, pp. 389-400 (1999)
Sirkia et al., "Use of hydrophilic polymers to control drug release from press-coated oxybutynin hydrochloride tablets", S.T.P. Pharma Sciences, vol. 3, No. 6, pp. 453-458 (1993).
Sist et al., "Experience with gabapentin for neuropathic pain in the head and neck: report of ten cases", Regional Anesthesia, vol. 22, No. 5, pp. 473-478 (1997).
Sivenius et al., "Double-blind study of gabapentin in the treatment of partial seizures", Epilepsia, vol. 32, pp. 539-542 (1991).
Solaro et al., "Gabapentin is effective in treating nocturnal painful spasms in multiple sclerosis", Multiple Sclerosis, vol. 6, pp. 192-193 (2000).
Soliman et al., "Gabapentin treatment for cocaine dependence in methadone-maintained opiod-dependent patients", Drug Alcohol Depend., vol. 60, Supp. 1, Abst. #S208 (2000).
"Specific delivery to the gastrointestinal tract", *Polymeric Site-specific Pharmacotherapy*, Domb, ed., John Wiley & Sons, Ltd., Chichester, West Sussex, England, pp. 282-283 (1994).
Stevenson et al., "Contrasting nutrient effects on the plasma level of an amino acid-like antiepileptic agent from jejunal administration in dogs", J. Pharm. Sci., vol. 86, No. 8, pp. 963-957 (1997).
Stevenson et al., "Colonic Absorption of Antiepileptic Agents", Epilepsia, vol. 33, pp. 63-67 (1997).
Stewart et al., "A saturable transport mechanism in the intestinal absorption of gabapentin in the underlying cause of the lack of proportionality between increasing dose and drug levels in plasma", Pharmac Res., vol. 10, pp. 276-281 (1993).
*The Pill Book*, 8th Edition, Silverman, ed., Bantam Books, New York, pp. B-C, J-K (1998).
Thomson et al., "Pharmacokinetics optimization of anticonvulsant therapy", Clin. Pharmacokinet., vol. 23, pp. 216-230 (1992).
Timmermans et al., "The cutoff size for gastric emptying of dosage", J. Pharm. Sci., vol. 82, No. 8, pp. 854 (1993).
Timmermans and Möes, "Factors controlling the buoyancy and gastric retention capabilities of floating matrix capsules: new data for reconsidering the controversy", J. Pharm. Sci., vol. 83, No. 1, pp. 18-24 (1994).
Timmins et al., "Optimization and characterization of a pH-independent extended-release hydrophilic matrix tablet", Pharmacuetical Development & Technology; vol. 2, No. 1, pp. 25-31 (1997).
Tomson, "Therapeutic monitoring of the new antiepileptic drugs", Eur. J. Clin. Pharmacol., vol. 55, pp. 697-705 (2000).
Tremont-Lukats et al., "Anticonvulsants for neuropathic pain syndromes: mechanisms of action and place in therapy", Drugs, vol. 60, No. 5, pp. 1029-1052 (2000).
Upton, "Mechanisms of action of new antiepileptic Drugs: rational design and serendipitous findings", Tips, vol. 15, pp. 456-463 (1994).
Vollmer, "Pharmacokinetics and metabolism of gabapentin in rat, dog and man", Arnzeim-Forsch/Drug Res., vol. 36, pp. 830-839 (1986).
Vollmer et al., "Summary of neurontin (gabapentin) clinical pharmacokinetics", Epilepsia, vol. 33, Suppl. 3, pp. 77 (1992).
Wang et al., "The simultaneous estimation of the influx and efflux blood-brain barrier permeabilities of gabapentin using a microdialysis-pharmacokinetic approach", Pharmac. Res., vol. 13, pp. 398-403 (1996).

(56) References Cited

OTHER PUBLICATIONS

Welling and Barbhajya, "Influence of Food and Fluid Volume on Chlorothiazide Bioavailability: Comparison of Plasma and Urinary Excretion Methods", J. Pharm. Sci., vol. 71, pp. 32-35 (1982).

Welling, "Interactions affecting drug absorption", Clin. Pharmacokinet., vol. 9, No. 5, pp. 404-434 (1984).

Wesche et al., "A pharmacokinetic comparison of pregabalin and gabapentin", J. Pain, vol. 6, No. 3, (2005) abstract only.

Wheeler, "Gabapentin", Current Opinion in Investigational Drugs, vol. 3, No. 3, pp. 470-477 (2002).

White, "Comparative anticonvulsant and mechanistic profile of the established and newer antiepileptic drugs", Epilepsia, vol. 40, No. 5, pp. S2-S10 (1999).

Wilding et al., "Relationship Between Systemic Drug Absorption and Gastrointestinal Transit After the Simultaneous Oral Administration of Carbamazepine as a Controlled-Release System and as a Suspension of $^{15}$N-Labelled Drug to Healthy Volunteers", Br. J. Clin Pharmac., vol. 32, pp. 573-579 (1991).

Wolf et al., "Gabapentin toxicity in children manifesting as behavioral changes," Epilepsia, vol. 36, pp. 1203-1205 (1996).

Wong et al., "Adverse reactions to new anticonvulsant drugs", Drug Safety, vol. 239, pp. 35-56 (2000).

Wong et al., "Clinical research, the long-term use of gabapentin, lamotrigine and vigabatrin in patients with chronic epilepsy", Epilepsia, vol. 40, pp. 1439-1445 (1999).

Wong et al., "Disposition of gabapentin in anuric subjects on hemodialysis", J. Clin. Pharmacol., vol. 35, pp. 622-626 (1995).

Zylicz, "Painful gynecomastia: an unusual toxicity of gabapentin", Letters, vol. 20, pp. 2-3 (2000).

GASTRIC RETENTIVE GABAPENTIN DOSAGE FORMS AND METHODS FOR USING SAME

RELATED APPLICATIONS

This application is a continuation of pending U.S. application Ser. No. 12/331,184, filed Dec. 9, 2008, which is a continuation of U.S. application Ser. No. 11/648,134, filed Dec. 29, 2006, now abandoned, which is a continuation-in-part of pending U.S. Ser. No. 11/322,448, filed Dec. 29, 2005, all of which are incorporated herein by reference in their entirety.

FIELD OF THE INVENTION

The invention relates to gastric retentive gabapentin dosage forms and methods of using them to reduce or eliminate gabapentin-induced side effects. For example, the dosage forms of the invention can be used to reduce or eliminate the side effects associated with treatment of non-nociceptive pain states.

BACKGROUND OF THE INVENTION

Gabapentin (1-(aminomethyl)cyclohexane acetic acid) is a 3-substituted γ-aminobutyric acid ("GABA") analog that was approved in the United States on Dec. 30, 1993 as NEURONTIN® (Pfizer Inc., New York, N.Y.), an immediate release dosage form of gabapentin for use as adjunctive therapy in the treatment of partial seizures in children and adults, and was subsequently approved for treatment of post-herpetic neuralgia ("PHN") in adults. In addition to seizures and PHN, gabapentin has also been used in the treatment of neuropathic pain, restless legs syndrome, essential tremor, bipolar disorder, migraine headaches, and the symptoms associated with menopause, hormonal imbalances, and chemotherapy. Magnus et al., EPILEPSIA 40:S66-S72 (1999); U.S. Pat. No. 6,310, 098 to Guttuso. Gabapentin is currently available as immediate release NEURONTIN® in 100 mg, 300 mg, and 400 mg hard shell capsules; 600 mg and 800 mg film-coated tablets; and in a liquid formulation having 250 mg/5 mL. The recommended dosage for gabapentin is a total daily dose of 900 mg to 1800 mg t.i.d. (i.e., three times daily).

In humans, gabapentin is absorbed throughout the small intestine with diminished absorption in the colon. The absorption of immediate release gabapentin occurs relatively slowly with the peak plasma concentration occurring approximately 2 to 3 hours after dosing. The oral bioavailability of gabapentin is dose-dependent, with approximately 60% bioavailability for a dose in the range of 300-400 mg, but with only 35% bioavailability for a dose of 1600 mg. Bourgeois, EPILEPSIA 36 (Suppl. 5):S1-S7 (1995); Gram, EPILEPSIA 37 (Suppl. 6):S12-S16 (1996); DRUGS OF TODAY 31:613-9:975-82 (1995); NEUROLOGY 44(Suppl. 5): S17-S32 (2003). The decrease in bioavailability with increasing dose of the immediate release tablet has been attributed to partially carrier-mediated absorption. Stewart, et al., PHARMACEUTICAL RESEARCH 10(2):276-281 (1993).

Food has only a small effect on the rate and extent of immediate release gabapentin absorption. Further, only 3% of circulating gabapentin is bound to plasma proteins. Gabapentin is not appreciably metabolized in humans, does not induce hepatic enzymes, and is eliminated unchanged by renal excretion with a half-life of 5-7 hours regardless of whether the drug is taken in a single dose or in multiple doses. (Chadwick; LANCET 343:89-91 (1994); Thomson, et al., CLIN. PHARMACOKINET. 23(3):216-230 (1992); and Riva, et al., CLIN. PHARMACOKINET. 3 1(6):470-493 (1996)).

Because gabapentin is administered t.i.d., patient compliance with the conventional immediate release dosage forms of the drug is an issue. In this respect, controlled release dosage forms that would lower the number of daily dosings of gabapentin to once-daily or twice-daily dosings would provide a significant advantage over the conventional immediate release dosage form; however, in order for the controlled release dosage form to be effective, the dosage form must overcome the poor absorption of the drug in the lower gastrointestinal tract.

In addition to the compliance and bioavailability issues associated with the conventional immediate release dosage form of gabapentin, gabapentin use also suffers from the adverse side effects associated with the drug. Side effects reported from gabapentin use include, most commonly, somnolence and dizziness, and to a lesser degree, fatigue, ataxia, weight gain, peripheral edema, diarrhea, headache, dry mouth, and blurred vision. More recently, gabapentin use has been associated with the serious side effect of reversible visual field constriction. Bekkelund et al., BRIT. MED. J 323: 1193 (2006).

The issue of gabapentin side effects has become increasingly troublesome since gabapentin was found to reduce the frequency and severity of hot flashes in menopausal women. U.S. Pat. No. 6,310,098 to Guttuso. As a result of the prevalence of the somnolence and dizziness side effects, many women who have been taking gabapentin for treatment of their menopausal symptoms have been forced to discontinue use of the drug.

In order for gabapentin to gain widespread acceptance for current, i.e., epilepsy and post-herpetic neuralgia, and future off-label uses, such as, for example, restless-leg syndrome, diabetic neuropathy, back pain, essential tremor, bipolar disorder, migraine prophylaxis, potentially alcohol and drug withdrawal, and the symptoms associated with menopause, hormonal imbalances, and chemotherapy, there is a need in the art for an improved dosage form of gabapentin that may be administered once or twice daily with sufficient absorption of the active agent to produce the desired therapeutic effects while increasing the bioavailability of the drug at elevated doses and reducing the side effects associated with the drug at the therapeutic dosages.

Examples of modified release dosage forms, such as controlled-release dosage forms, sustained release dosage forms, and extended release dosage forms are known in the art to which the invention pertains; however, to the best of the inventor's knowledge, gabapentin has not been successfully incorporated into any modified release dosage form because the pharmacokinetics of the drug does not facilitate the absorption of the drug in modified release dosage forms. In fact, the innovator noted in the Summary Basis of Approval (NDA 20-235), that a pilot study (Study #877-076) of a 600 mg sustained release formulation "indicated unacceptable sustained release characteristics," (NDA 20-235) which was attributed to decreasing rate and extent of absorption as gabapentin "moves lower in the GI tract." (NDA 20-235). In order to overcome the shortcomings inherent in the immediate delivery dosage forms of gabapentin, a gastric retentive dosage form of gabapentin would allow for sustained release of gabapentin while avoiding the significant loss of bioavailability of the drug observed with non-gastric retentive controlled release dosage forms.

Pain management continues to be a challenge for medical practitioners. Many pain medications have unfavorable side effects. In addition, patients can develop tolerance to pain medications and require larger doses to reach a previously achieved level of pain relief.

Pain is generally classified as either nociceptive pain or non-nociceptive pain. Nociceptive pain arises from the stimulation of pain receptors (i.e., nociceptive receptors) to heat, cold, vibration, stretch, and chemical stimulus from damaged cells. Somatic pain (i.e., musculoskeletal pain, such as pain specific to skin, muscle, joints, bones, and ligaments) and visceral pain (i.e., pain specific to the internal organs and main body cavities) are the two types of nociceptive pain. Nociceptive pain is usually time-limited and thus, when the tissue heals, the pain is resolved. During periods of pain, nociceptive pain responds well to treatment with opioids.

Non-nociceptive pain arises from within the peripheral and central nervous system, where there are no pain receptors. The pain associated with non-nociceptive pain is generated from nerve cell dysfunction. Non-nociceptive pain includes neuropathic pain and sympathetic pain.

Neuropathic pain originates in the peripheral nervous system (the nerves between the tissue and the spinal cord) or the central nervous system (the nerves between the spinal cord and the brain). Neuropathic pain may be caused by nerve degeneration (e.g., by multiple sclerosis), nerve pressure (e.g., from a trapped nerve); nerve inflammation (e.g., from a torn or slipped disc), or nerve infection (e.g., from shingles or other viral infections). With neuropathic pain, the injured nerves become electrically unstable firing of signals in an inappropriate, random, and disordered fashion. Neuropathic pain is characterized by nerve malfunctions such as hypersensitivity to touch, vibrations, and extreme temperatures and is often described as burning, lancinating, and shooting pain.

Sympathetic pain is caused from possible over activity of the sympathetic system, which controls blood flow to tissues such as skin and muscle, sweating by the skin, and the speed and responsiveness of the peripheral nervous system. Sympathetic pain occurs most commonly after fractures and soft tissue injuries of the arms and legs. Sympathetic pain is characterized by extreme sensitivity in the skin surrounding the site of injury and peripherally in the afflicted limb, which may become so painful that the patient will refuse to use it causing secondary problems with the limb due to non-use.

Unlike nociceptive pain is not time limited and is not easily treatable. Non-nociceptive pain is generally treated with antidepressants, anti-convulsants (i.e., anti-epileptic drugs), and anti-arrhythmics; however, to date, there is no effective treatment for non-nociceptive pain. In commonly owned co-pending U.S. patent application Ser. No. 10/280,309 (Publication No. US 2003/0100611 A1), the present inventors disclosed a gastric-retentive form of gabapentin and the use of the drug for the treatment of neuropathic pain, which is a non-nociceptive pain state.

An osmotic dosage form has been described for delivery of gabapentin prodrugs. U.S. Pat. No. 6,683,112 to Chen at al. describes sustained release formulations that deliver gabapentin prodrugs by means of the push-pull osmotic pump system described in U.S. Pat. No. 4,612,008 to Wong et al. This system however, is not a gastric retentive dosage form and would be expected to deliver the drug with poor bioavailability.

Examples of gastric retentive dosage forms are described in U.S. Pat. No. 4,996,058 to Sinnreich; U.S. Pat. No. 5,232,704 to Franz et al.; U.S. Pat. No. 6,120,802 to Wong et al.; and commonly owned U.S. Pat. No. 5,972,389 to Shell et al. and PCT Publication No. WO 98/055107 to Depomed, Inc. None of these references, however, teach or suggest the use of the gastric retentive dosage forms described therein for the administration of gabapentin. To the best of the inventors' knowledge, a dosing regimen using a gastric retentive dosage form of gabapentin for reducing or eliminating side effects associated with gabapentin treatment has not been previously described. Further, to the best of the inventors' knowledge, a dosing regimen using a gastric retentive dosage form of gabapentin for pain treatment has not been previously described.

The present invention overcomes the need in the art for a more effective gabapentin dosage form that will increase patient compliance and provide for extended effective plasma levels so that patients suffering from a non-nociceptive pain state may be able to more effectively use gabapentin for treatment of pain symptoms.

SUMMARY OF THE INVENTION

The present invention overcomes the need in the art for an improved dosage form of gabapentin by providing a gastric retentive dosage form of gabapentin that overcomes the compliance, bioavailability, and side effect issues associated with the conventional immediate release dosage forms of gabapentin.

The gastric retentive oral dosage form of the present invention has the advantage of requiring only once or twice daily closings; thus improving patient compliance. Further, if the decreased bioavailability at all doses of controlled-release gabapentin dosage forms were due to lack of colonic absorption, then the gastric retentive gabapentin dosage form of the present invention has the additional advantage of keeping the drug in the region of absorption for a longer period of time; thus improving the bioavailability of the drug. Moreover, gabapentin has saturable absorption and thus, a gastric retentive dosage form of gabapentin by virtue of its slower release rate should allow better absorption at higher doses. This improved bioavailability with increasing dose allows higher doses of the drug to be given at once to permit once or twice daily dosing. This also allows the timing of the high dose to be in the evening to minimize side effects that may be a problem during the day, but not at night, such as somnolence. Furthermore, the slower release rate allows for a slower rise in peak plasma levels, which may be associated with side effects.

In one embodiment of the invention, there is provided a method of reducing or eliminating side effects associated with gabapentin use, comprising administering a therapeutically effective amount of gabapentin in a gastric retentive dosage form to a patient in a once-daily dosing regime within a single 24 hour period.

In another embodiment of the invention, there is provided a method of reducing or eliminating side effects associated with gabapentin use, comprising administering a therapeutically effective amount of gabapentin in a gastric retentive dosage form to a patient in a twice-daily dosing regimen within a single 24 hour period.

Examples of side effects that may be reduced or eliminated with the gastric retentive gabapentin dosage form of the present invention include without limitation, somnolence, dizziness, fatigue, ataxia, weight gain, peripheral edema, diarrhea, headache, dry mouth, blurred vision, and/or reversible visual field constriction.

With both the once-daily and twice-daily dosing regimens, upon administration of the gastric retentive dosage form to the patient, the patient's blood plasma exhibits a maximum concentration ($C_{max}$) of gabapentin that is approximately 15% to approximately 85% less than $C_{max}$ for a comparable dose of immediate release gabapentin. For example the maximum concentration ($C_{max}$) of gabapentin that is approximately 20, 25, 30, 35%, 40%, 45%, 50%, 55%, 60%, 65%, 70%, 75%, 80% less than $C_{max}$ for a comparable dose of immediate release gabapentin. The time to $C_{max}$ ($T_{max}$) is approximately 1.5 to approximately 5, alternatively, time to $C_{max}$ ($T_{max}$) is approximately 1.5 to approximately 3.5, hours longer (equivalent to approximately 40% to approximately 80% slower) than $T_{max}$ for a comparable dose of immediate release gabapentin. For example, the time to $T_{max}$ is approximately 2, 2.5, 3, 3.5, 4, 4.5 hours longer that the $T_{max}$ for a comparable dose of immediate release gabapentin. The bioavailability (AUC) should be at least 70%, 75%, 80%, 85%, 90%, 95%, 96%, 97%, 98% 99% of the AUC, or greater than AUC achieved from a comparable dose of an immediate release dosage form and should show greater bioavailability than the immediate release dosage forms at higher doses, in particular, at 2400 mg an AUC that is approximately equal to or greater than AUC for a comparable dose of immediate release gabapentin. In some cases the AUC may be up to 150% or more of the AUC achieved from a comparable dose of an immediate release dosage form.

The gastric retentive dosage forms of the present invention may be used for any disease state or condition that may be treated with conventional immediate release gabapentin, such as for example, seizures, PHN (post hepatic neuralgia), diabetic peripheral neuropathy ("DPN"), pain, restless-leg syndrome, essential tremor, bipolar disorder, migraine prophylaxis, and the symptoms associated with hormonal imbalances and chemotherapy as well as potentially for alcohol or drug withdrawal. Within the context of symptoms associated with hormonal imbalances, such symptoms include menopausal hot flashes. Within the context of the symptoms associated with chemotherapy, such symptoms include chemotherapy-induced hot flashes and nausea.

For example, gastric retentive dosage forms of gabapentin that may be administered to a patient suffering from a pain state in once or twice daily administrations. The pain states that may be treated by the gastric retentive dosage forms of the present invention include non-nociceptive pain states, such as neuropathic pain or sympathetic pain or pain states that include a combination of non-nociceptive pain and nociceptive pain.

In one embodiment of the invention, there is provided a method of treating a patient suffering from a pain state comprising administering to the patient a gastric retentive dosage form comprised of a therapeutically effective amount of gabapentin, wherein the dosage form is administered to the patient in a once-daily dosing regimen within a single 24-hour period.

In another embodiment of the invention, there is provided a method of treating a patient suffering from a pain state comprising administering to the patient a gastric retentive dosage form comprised of a therapeutically effective amount of gabapentin, wherein the dosage form is administered to the patient in a twice-daily dosing regimen within a single 24-hour period.

In one embodiment, the combination of dosing in a once-daily or twice daily dosing regimen with gastric retentive gabapentin allows for a patient to obtain efficacy in pain or some other condition for which the gabapentin has been administered due to the unique combination of the gastric retentive dosage form, allowing for extended delivery without significant loss in bioavailability, dosing once daily with the evening meal or asymmetric dosing with the higher dose in the evening, allowing for the potential to ameliorate side effects and thus titrate to a more efficacious dose, and the enhanced bioavailability of the gastric retentive dosage form at higher doses compared to the same single dose of an immediate release gabapentin dosage form such as NEURONTIN® capsules or tablets. As noted above, a gastric retentive dosage form allows for extended delivery without loss in bioavailability, thus prolonging the plasma concentrations of the drug. Further, the slower delivery obtained from the gastric retentive dosage form prevents or ameliorates the impact of saturation of the carrier-mediated absorption allowing a higher percent absorption at the higher dose levels. In addition, the dosing regimen, either once daily in the evening or twice daily with the higher dose in the evening may decrease or ameliorate side effects, allowing the patient to tolerate a higher dose, and due to the gastric retentive controlled delivery, is absorbed better than the equivalent dose of immediate release gabapentin if administered as a single dose at the same dose. Thus, the combination of gastric retention of gabapentin, the avoidance or amelioration of impacts of the carrier-mediated saturation, as well as the once-daily or twice daily asymmetric dosing, allows for the subject to obtain efficacy for pain or some other indication for which the gabapentin is being administered.

The invention relates to a method of treating a patient suffering from a pain state by administering a therapeutically effective amount of a GABA analog in a gastric retentive dosage form to a patient in a once-daily dosing regimen within a single 24 hour period.

The invention also relates to a method of treating a patient suffering from a pain state by administering a therapeutically effective amount of a GABA analog in a gastric retentive dosage form to a patient in a twice-daily dosing regimen within a single 24 hour period.

Further, the invention relates to a method of reducing or eliminating side effects associated with γ-aminobutyric acid (GABA) analogs by administering a therapeutically effective amount of a GABA analog in a gastric retentive dosage form to a patient in a once-daily dosing regimen within a single 24 hour period.

Further, the invention relates to a method of reducing or eliminating side effects associated with γ-aminobutyric acid (GABA) analogs by administering a therapeutically effective amount of a GABA analog in a gastric retentive dosage form to a patient in a twice-daily dosing regimen within a single 24 hour period.

For example, the GABA analog is gabapentin. In other examples, the GABA analog is pregablin.

In one embodiment, the therapeutically effective amount of gabapentin is to be administered to the patient in a total daily dose ranging from approximately 300 mg to approximately 9600 mg.

In one embodiment, individual dosage units of the gastric retentive dosage form are approximately 100 mg to approximately 1800 mg of gastric retentive gabapentin.

In some embodiments, the dosage form is to be administered to the patient in an evening dose in fed mode.

For example, the dosage form is a tablet or capsule.

In one embodiment, the invention relates to a method of treating a patient suffering from menopause-related hot flashes.

In one embodiment, the method of the invention is used to treat a patient suffering from side effects such as somnolence, dizziness, fatigue, ataxia, weight gain, peripheral edema, diarrhea, headache, dry mouth, blurred vision, and reversible visual field constriction.

For example, the side effects are somnolence and/or dizziness.

In one embodiment, the method of the invention is used to treat a patient suffering from a pain state that is a mixture of non-nociceptive pain and nociceptive pain.

In one embodiment, the pain state is a non-nociceptive pain. For example, the non-nociceptive pain is neuropathic pain.

The neuropathic pain is, for example, diabetic neuropathy, HIV sensory neuropathy, postherpetic neuralgia, post-thoracotomy pain, trigeminal neuralgia, radiculopathy, neuropathic pain associated with chemotherapy, reflex sympathetic dystrophy, back pain, peripheral neuropathy, entrapment neuropathy, phantom limb pain, or complex regional pain syndrome.

In one embodiment, the method of the invention is used to treat a patient suffering from a pain state that is a mixture neuropathic pain and sympathetic pain. For example, the pain state is a migraine headache. For example, the non-nociceptive pain is selected from pain associated with post-menopausal symptoms or pain associated with chronic pelvic pain syndrome.

In one embodiment, the method of the invention is used to treat a patient suffering from chemotherapy-related hot flashes and/or nausea.

In one embodiment, upon administration, bioavailability (AUC) of the GABA analogue at 2400 mg is approximately 70% to approximately 130% of the AUC for a comparable total daily dose of immediate release gabapentin.

In another embodiment, upon administration, bioavailability (AUC) of the GABA analogue at 2400 mg is approximately 80% to approximately 150% of the AUC for a comparable total daily dose of immediate release gabapentin.

In another embodiment, upon administration, bioavailability (AUC) of the GABA analogue at 2400 mg is approximately 100% to approximately 150% of the AUC for a comparable total daily dose of immediate release gabapentin.

In another embodiment, upon administration, bioavailability (AUC) of the GABA analogue at 1800 mg is approximately 70% to approximately 130% of the AUC for a comparable total daily dose of immediate release gabapentin.

In another embodiment, upon administration, bioavailability (AUG) of the GABA analogue at 1800 mg is approximately 80% to approximately 150% of the AUC for a comparable total daily dose of immediate release gabapentin.

In another embodiment, upon administration, bioavailability (AUC) of the GABA analogue at 1800 mg is approximately 100% to approximately 150% of the AUC for a comparable total daily dose of immediate release gabapentin.

In one embodiment, administration to a patient as a single dose, results in blood plasma levels of the patient that exhibit a maximum concentration ($C_{max}$) of the GABA analogue that is approximately 15% to approximately 85% less than $C_{max}$ for a comparable single dose of immediate release gabapentin.

In another embodiment, administration to a patient as a single dose results in blood plasma levels of the patient that exhibit a maximum concentration ($C_{max}$) of the GABA analogue that is approximately 35% to approximately 85% less than $C_{max}$ for a comparable single dose of immediate release gabapentin.

In another embodiment, administration to a patient as a single dose results in blood plasma levels of the patient that exhibit a maximum concentration ($C_{max}$) of the GABA analogue that is approximately 30% to approximately 50% less than $C_{max}$ for a comparable single dose of immediate release gabapentin.

In another embodiment, administration to a patient as a single dose results in time to $C_{max}$ ($T_{max}$) of gabapentin that is approximately 1.5 to approximately 5 hours longer than $T_{max}$ for a comparable single dose of immediate release gabapentin.

In another embodiment, administration to a patient as a single dose results in time to $C_{max}$ ($T_{max}$) of gabapentin that is approximately 1.5 to approximately 3.5 hours longer than $T_{max}$ for a comparable single dose of immediate release gabapentin.

In one embodiment, the patient is further treated with an additional active agent selected from anticonvulsants, tricyclic antidepressants, opioids, and secondary analgesics. For example, the additional active agent is administered in the same gastric retentive dosage form as the GABA analog.

For example, the anticonvulsants can be carbamazepine, phenyloin, or lamotrigine.

For example, the tricyclic antidepressants are selected from amitriptyline, imipramine, clomipramine, and desipramine.

For example, the opioids are selected from oxycodone and tramadol.

For example, the secondary analgesic is a non-steroidal anti-inflammatory drug.

In one embodiment, the dosage form is administered to the patient in fed mode in a morning dose and an evening dose.

In one embodiment, the morning dose is less than the evening dose.

For example, the morning dose is equal to or less than about one-half of the evening dose. For example, the morning dose is equal to or less than about one-third of the evening dose. For example, the morning dose is equal to or less than about one-quarter of the evening dose.

The invention relates to a method of reducing or eliminating side effects associated with γ-aminobutyric acid (GABA) analogs by administering a therapeutically effective amount of a GABA analog in a gastric retentive dosage form to a patient in a once-daily dosing regimen within a single 24 hour period or in a twice daily dosing regimen in which the dose in the morning and dose in the evening are not equal, also within a single 24 hour period, and wherein upon administration to a patient as a single dose results in blood plasma levels of the patient that exhibit a maximum concentration ($C_{max}$) of gabapentin that is approximately 15% to approximately 85% less than $C_{max}$ for a comparable dose of immediate release gabapentin also administered as a single dose, and wherein upon administration, bioavailability (AUC from 0 to 24 hours at steady-state) of the gabapentin 2400 mg is approximately 80% to approximately 150% of the AUC for a comparable total daily dose of immediate release gabapentin.

In one embodiment administration to a patient as a single dose results in blood plasma levels of the patient that exhibit a maximum concentration ($C_{max}$) of gabapentin that is approximately 30% to approximately 50% less than $C_{max}$ for a comparable dose of immediate release gabapentin also administered as a single dose.

The invention relates to a method of reducing or eliminating side effects associated with γ-aminobutyric acid (GABA) analogs by administering a therapeutically effective amount of a GABA analog in a gastric retentive dosage form to a patient in a once-daily dosing regimen within a single 24 hour period or in a twice daily dosing regimen in which the dose in the morning and dose in the evening are not equal, also within a single 24 hour period, and wherein administration to a patient as a single dose results in blood plasma levels of the patient that exhibit a maximum concentration ($C_{max}$) of gabapentin that is approximately 15% to approximately 85% less than $C_{max}$ for a comparable dose of immediate release gabapentin also administered as a single dose, and wherein upon administration, bioavailability (AUC from 0 to 24 hours at steady-state) of the gabapentin at 1800 mg is approximately 80% to approximately 150% of the AUC for a comparable total daily dose of immediate release gabapentin.

In one embodiment, administration to a patient as a single dose, results in blood plasma levels of the patient that exhibit a maximum concentration ($C_{max}$) of gabapentin that is approximately 30% to approximately 50% less than $C_{max}$ for a comparable dose of immediate release gabapentin also administered as a single dose.

The invention relates to a method of treating a patient suffering from a pain state by administering a therapeutically effective amount of a GABA analog in a gastric retentive dosage form to a patient in a once-daily dosing regimen within a single 24 hour period or in a twice daily dosing regimen in which the dose in the morning and dose in the evening are not equal, also within a single 24 hour period, and wherein administration to a patient as a single dose results in blood plasma levels of the patient that exhibit a maximum concentration ($C_{max}$) of gabapentin that is approximately 15% to approximately 85% less than $C_{max}$ for a comparable dose of immediate release gabapentin also administered as a single dose, and wherein upon administration, bioavailability (AUC from 0 to 24 hours at steady-state) of the gabapentin at 2400 mg is approximately 70% to approximately 150% of the AUC for a comparable total daily dose of immediate release gabapentin.

For example, administration to a patient as a single dose, results in blood plasma levels of the patient that exhibit a maximum concentration ($C_{max}$) of gabapentin that is approximately 30% to approximately 50% less than $C_{max}$ for a comparable dose of immediate release gabapentin also administered as a single dose.

The invention relates to a method of treating a patient suffering from a pain state by administering a therapeutically effective amount of a GABA analog in a gastric retentive dosage form to a patient in a once-daily dosing regimen within a single 24 hour period or in a twice daily dosing regimen in which the dose in the morning and dose in the evening are not equal, also within a single 24 hour period, and wherein administration to a patient as a single dose results in blood plasma levels of the patient that exhibit a maximum concentration ($C_{max}$) of gabapentin that is approximately 15% to approximately 85% less than $C_{max}$ for a comparable dose of immediate release gabapentin also administered as a single dose, and wherein upon administration, bioavailability (AUC from 0 to 24 hours at steady-state) of the gabapentin at 1800 mg is approximately 70% to approximately 150% of the AUC for a comparable total daily dose of immediate release gabapentin.

For example, administration to a patient as a single dose results in blood plasma levels of the patient that exhibit a maximum concentration ($C_{max}$) of gabapentin that is approximately 30% to approximately 50% less than $C_{max}$ for a comparable dose of immediate release gabapentin also administered as a single dose.

In one embodiment, upon administration, bioavailability (AUC) of the GABA analogue at 1800 mg is approximately 70% to approximately 130% of the AUC for a comparable total daily dose of immediate release gabapentin.

In another embodiment, upon administration, bioavailability (AUC) of the GABA analogue at 1800 mg is approximately 80% to 150% of the AUC for a comparable total daily dose of immediate release gabapentin.

In one embodiment, upon administration, bioavailability (AUC) as measured over 24 hours of the GABA analogue at 1800 mg is approximately 80% to approximately 150% of the AUC for a comparable total daily dose of immediate release gabapentin.

DETAILED DESCRIPTION OF THE INVENTION

Definitions

Figure 1:
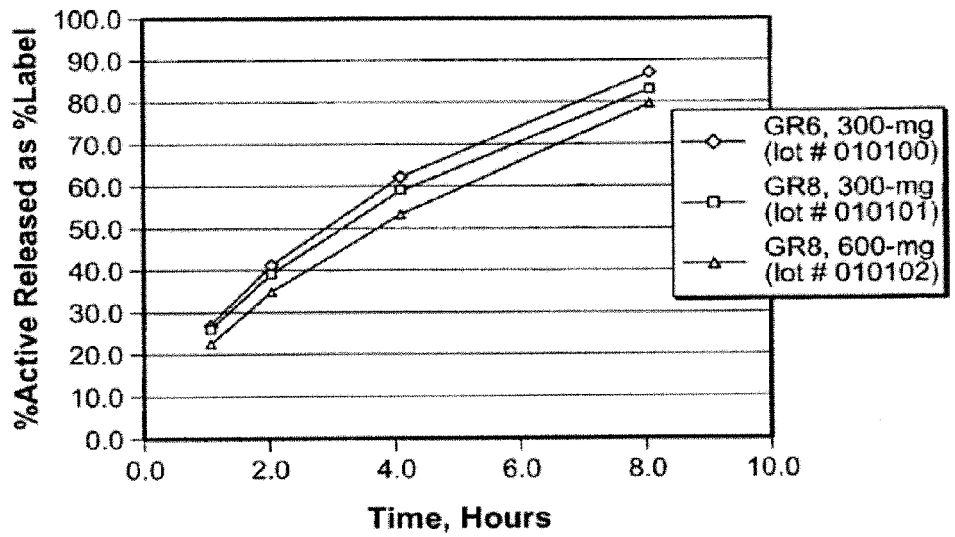
FIG. 1 illustrates the dissolution profiles for three gastric retentive gabapentin formulations.

Before describing the present invention in detail, it is to be understood that the terminology used herein is for the purpose of describing particular embodiments only, and is not intended to be limiting.

It must be noted that as used in this specification and the appended claims, the singular forms "a," "an" and "the" include plural referents unless the context clearly dictates otherwise; thus, for example, reference to "an active agent" or "a pharmacologically active agent" includes a single active agent as well a two or more different active agents in combination, reference to "a polymer" includes mixtures of two or more polymers as well as a single polymer, and the like.

In describing and claiming the present invention, the following terminology will be used in accordance with the definitions set out below.

The terms "effective amount" or a "therapeutically effective amount" refer to the amount of drug or pharmacologically active agent to provide the desired effect without toxic effects.

The terms "drug," "active agent," and "pharmacologically active agent" are used interchangeably herein to refer to any chemical compound, complex or composition that is suitable for oral administration and that has a beneficial biological effect, preferably a therapeutic effect in the treatment or prevention of a disease or abnormal physiological condition. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent," and "drug" are used, then, or when a particular active agent is specifically identified, it is to be understood that applicants intend to include the active agent per se as well as pharmaceutically acceptable, pharmacologically active salts, esters, amides, prodrugs, metabolites, analogs, etc.

The term "dosage form" refers to the physical formulation of the drug for administration to the patient. Dosage forms include without limitation, tablets, capsules, caplets, liquids, syrups, lotions, lozenges, aerosols, patches, enemas, oils, ointments, pastes, powders for reconstitution, sachets, solutions, sponges, and wipes. Within the context of the present invention, the gabapentin formulation will generally be administered to patients in the form of tablets or capsules, although a liquid formulation is also contemplated under the invention.

The term "dosage unit" refers to a single unit of the dosage form that is to be administered to the patient. The dosage unit will be typically formulated to include an amount of drug sufficient to achieve a therapeutic effect with a single administration of the dosage unit although where the size of the dosage form is at issue, more than one dosage unit may be necessary to achieve the desired therapeutic effect. For example, a single dosage unit of a drug is typically, one tablet, one capsule, or one tablespoon of liquid. More than one dosage unit may be necessary to administer sufficient drug to achieve a therapeutic effect where the amount of drug causes physical constraints on the size of the dosage form. For example, within the context of the gastric retentive gabapentin dosage form of the present invention, where the therapeutic effective amount of gabapentin is 1800 mg, the patient would be required to take multiple dosage units of gabapentin because a single dosage unit of 1800 mg of gabapentin would be too large for a patient to swallow without discomfort. In such a situation, the patient would take three 600 mg tablets or capsules or two 900 mg tablets or capsules of the gabapentin in order to achieve the 1800 mg therapeutic dose. It is to be understood that the dosage units of the gastric retentive gabapentin of the present invention is not restricted to any particular size dosage unit (such as the 600 and 900 mg tablets or capsules discussed above) and that any dosage unit of a size that would not be restrictive for comfortable ingestion is contemplated under the present invention. As an alternative to administering a plurality of 300-900 mg tablets or capsules, a large dose of gabapentin could be prepared in a single large dosage unit that is cut in half at the time of administration. Thus, with the 1800 mg therapeutic dose, a tablet of 1800 mg could be prepared that could be cut in half or in thirds in order to make the 1800 mg dosage unit more easily ingested.

"Total daily dose" is the total amount of drug administered to the patient in one 24 hour period, regardless of whether the protocol calls for a once-daily, twice-daily, or thrice-daily administration of the drug. Thus, the total amount of drug is summed for a given 24 hour period to determine how much total drug the patient is to be administered in a given day. For gabapentin, the maximum daily total dose deemed reasonable is about 9600 mg with the most common daily doses of gabapentin being in the range of 1800 mg to 2400 mg daily; however, it is to be understood that the amount of gabapentin to be administered to a particular patient will vary due to the extent of the patient's symptoms requiring treatment, the patient's tolerance for gabapentin or drugs in general, the size of the patient, and various other factors that one of ordinary skill in the art must take into consideration.

The term "asymmetric dose" refers to the administration of more than one unequal doses of a particular drug in a 24 hour period. For example, two asymmetric doses of a particular drug are administered in a 24 hour period. Asymmetric doses are typically administered as a small dose in the morning and a proportionally larger dose in the evening. Within the context of the present invention, a morning dose of the gastric retentive gabapentin of the present invention may be about one-half, one-third, or one-fourth the evening dose. Exemplary asymmetrical doses of the gastric retentive gabapentin of the present invention may be 600 mg in the morning and 1200 mg in the evening (1800 total daily dose), 800 mg in the morning and 1500 mg in the evening (2300 total daily dose), 1000 mg in the morning and 2400 mg in the evening (3400 total daily dose), 800 mg in the morning and 3600 mg in the evening (4400 total daily dose), or 600 mg in the morning and 6000 mg in the evening (6600 total daily dose). While an asymmetric dosing regimen for gabapentin will generally be administered with the smaller dose in the morning and the larger dose in the evening, there may be situations where the morning dose may need to exceed the evening dose for reasons based on the needs of the patient, the degree of the patient's symptoms, and other factors determined by the patient's physician.

By contrast, the term "symmetric dose" refers to the administration of two equal doses in a 24 hour period, such as for example, 300 mg of a given drug in the morning and 300 mg in the evening.

"Titration" is the process of ramping up the total daily amount of drug administered to the patient. "Titration" allows the patient's body to get used to the higher dose, and ensures that the patient is prepared for subsequent higher doses of the drug through a succession of daily doses that are of increasing amount. For example, with gabapentin, where the maintenance dose is 1500 mg, the titration protocol might be 300 mg the first day, 600 mg the second say, 900 mg the third day, 1200 mg the fourth day, and 1500 mg the fifth day. In this way, a titration schedule of 5 days can serve to adjust the patient to a maintenance dose of 1500 mg.

"Weaning," which is also referred to as "tapering," is the process of reducing the daily total dose a patient is receiving from the maintenance dose to a lesser dose. "Weaning" occurs when a patient is experiencing fewer of the symptoms requiring treatment or the treating physician would like to test whether the patient can reduce a maintenance dose. Weaning is effectively the opposite of titration, and occurs by successively reducing a daily maintenance dose to a lower level. Weaning can occur down to 0 mg of drug, depending on whether the patient is in fact ready to completely stop taking the medication.

"Maintenance" is the dosage amount that the patient needs to reach and maintain a desired level of relief from the symptoms under treatment. The maintenance dose is generally a daily dosage amount, such as, for example 1200 mg, 1500 mg, 1800 mg, or 2400 mg. The maintenance dose is generally titrated to and maintained for a designated period of time. As discussed above, maintenance doses may also be diminished by weaning. As is known by those of ordinary skill in the art, maintenance doses should be set to minimize any side effects of the drug.

The term "controlled release" is intended to refer to any dosage form in which release of the drug is not immediate, i.e., with a "controlled release" formulation, oral administration does not result in immediate release of the drug into an absorption pool. The term is used interchangeably with "non-immediate release" as defined in *Remington: The Science and Practice of Pharmacy,* 20th edition (Lippincott Williams & Wilkins, 2000). Examples of controlled release dosage forms include "delayed release," "sustained or extended release," and "modified release" dosage forms. As discussed therein, immediate and non-immediate release can be defined kinetically by reference to the following equation:

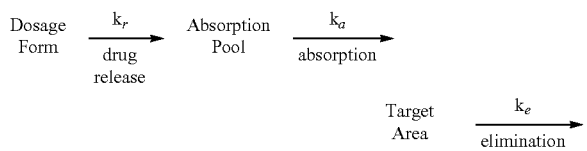

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area. It should be noted that this simplified model uses a single first order rate constant for release and absorption, and that the controlled release kinetics with any particular dosage form may be much more complicated. In general, however, the term "controlled release" as used herein includes any nonimmediate release formulation.

"Delayed release" dosage forms are a category of modified release dosage forms in which the release of the drug is delayed after oral administration for a finite period of time after which release of the drug is unhindered. Delayed release dosage forms are frequently used to protect an acid-labile drug from the low pH of the stomach or where appropriate to target the GI tract for local effect while minimizing systemic exposure. Enteric coating is frequently used to manufacture delayed release dosage forms.

The terms "sustained release," and "extended release" are used interchangeably herein to refer to a dosage form that provides for gradual release of a drug over an extended period of time. With extended release dosage forms, the rate of release of the drug from the dosage form is reduced in order to maintain therapeutic activity of the drug for a longer period of time or to reduce any toxic effects associated with a particular dosing of the drug. Extended release dosage forms have the advantage of providing patients with a dosing regimen that allows for less frequent dosing, thus enhancing compliance. Extended release dosage forms can also reduce peak-related side effects associated with some drugs and can maintain therapeutic concentrations throughout the dosing period thus avoiding periods of insufficient therapeutic plasma concentrations between doses.

The term "modified release" refers to a dosage form that includes both delayed and extended release drug products. The manufacture of delayed, extended, and modified release dosage forms are known to ordinary skill in the art and include the formulation of the dosage forms with excipients or combinations of excipients necessary to produce the desired active agent release profile for the dosage form.

The "gastric retentive" oral dosage forms described herein are a type of extended release dosage form. Gastric retentive dosage forms are beneficial for the delivery of drugs with reduced absorption in the lower GI tract or for local treatment of diseases of the stomach or upper GI tract. For example, in certain embodiments of gastric retentive oral dosage forms of the present invention, the dosage form swells in the gastric cavity and is retained in the gastric cavity of a patient in the fed med so that the drug may be released for heightened therapeutic effect. See, Hou et al., *Crit. Rev. Ther. Drug Carrier Syst.* 20(6):459-497 (2003).

Figure 2:
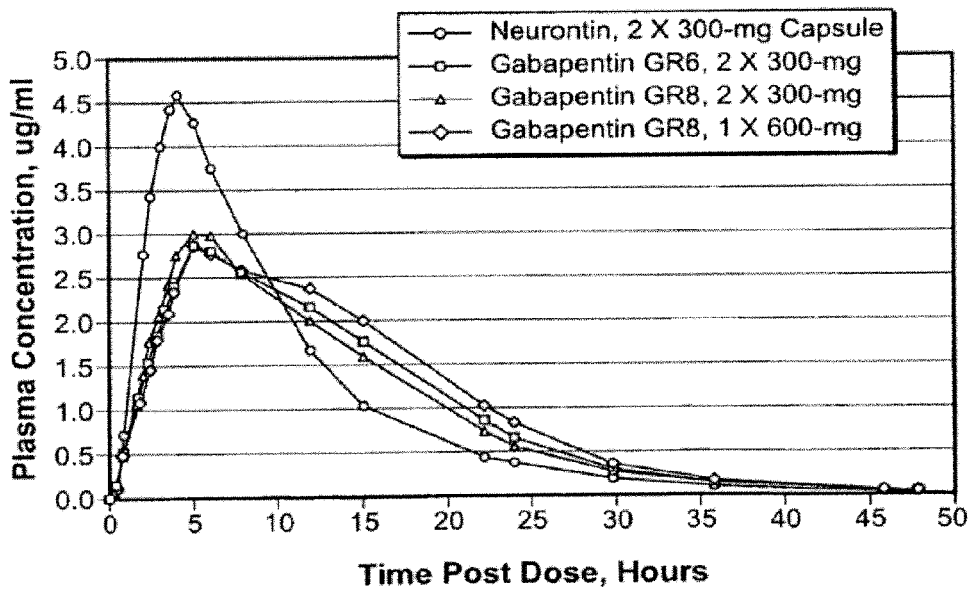
FIG. 2 illustrates the average plasma profile of three gastric retentive formulations and the immediate release gabapentin capsule dosage form sold under the trade name NEURONTIN®.
Figure 3:
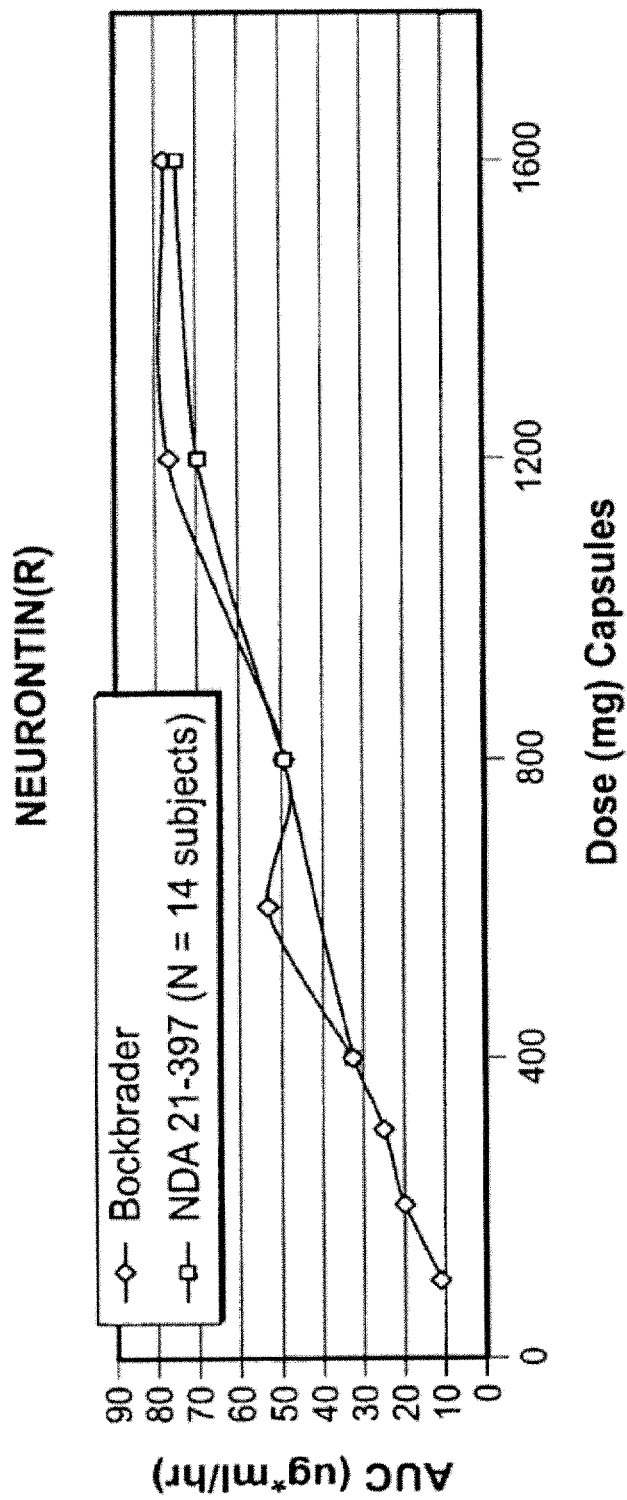
FIGS. 3 and 5 illustrate the in vivo AUC versus dose for immediate release NEURONTIN®.
Figure 4:
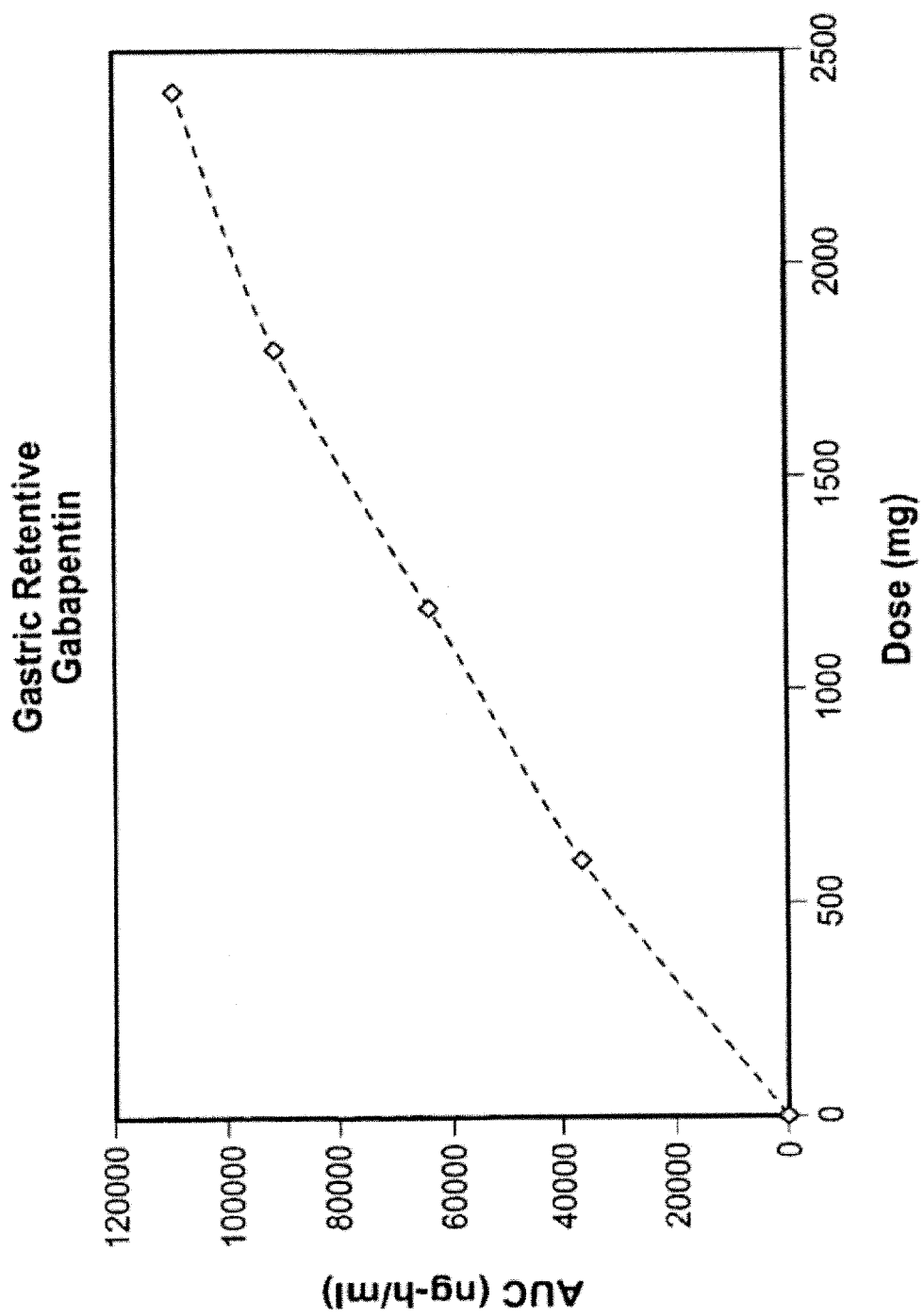
FIGS. 4 and 6 illustrate the in vivo AUC versus dose for the gastric retentive gabapentin dosage form of the present invention.
Figure 5:
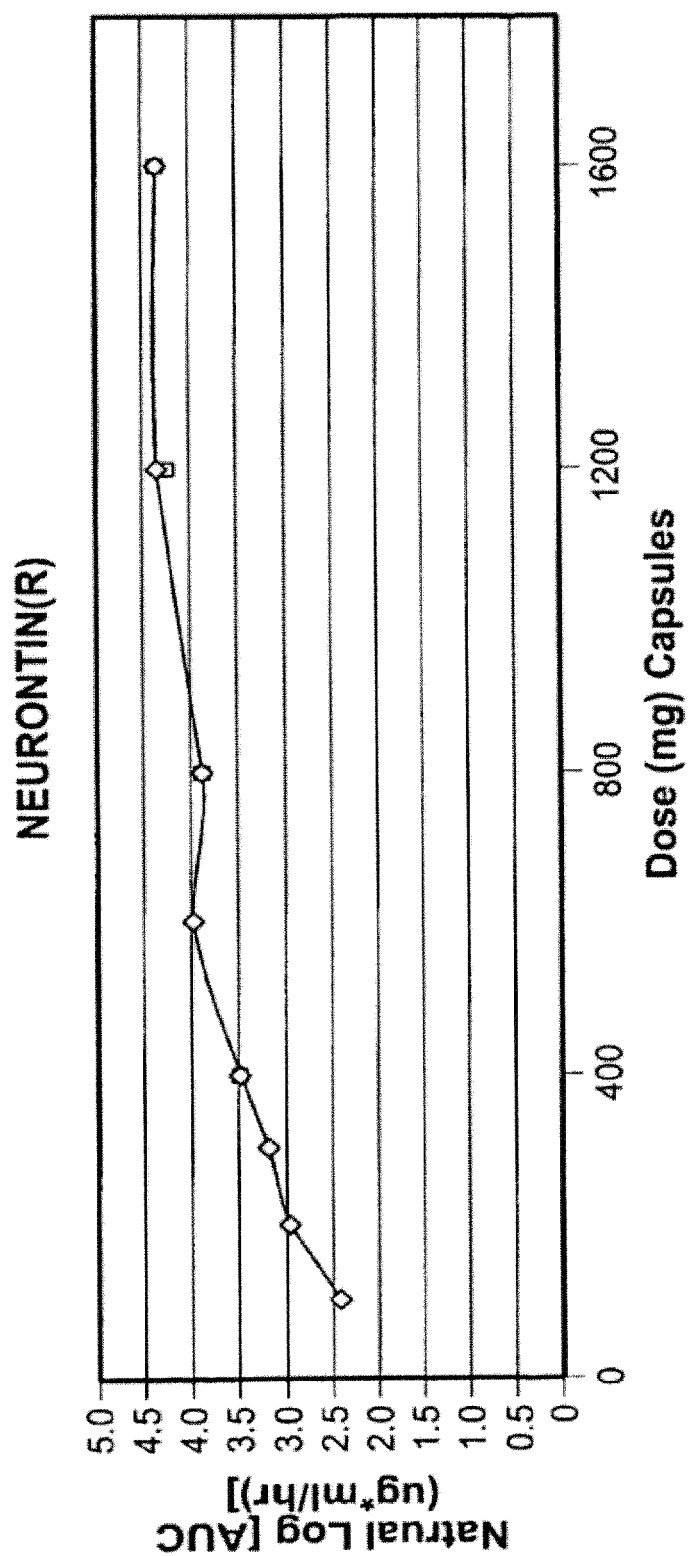
Figure 6:
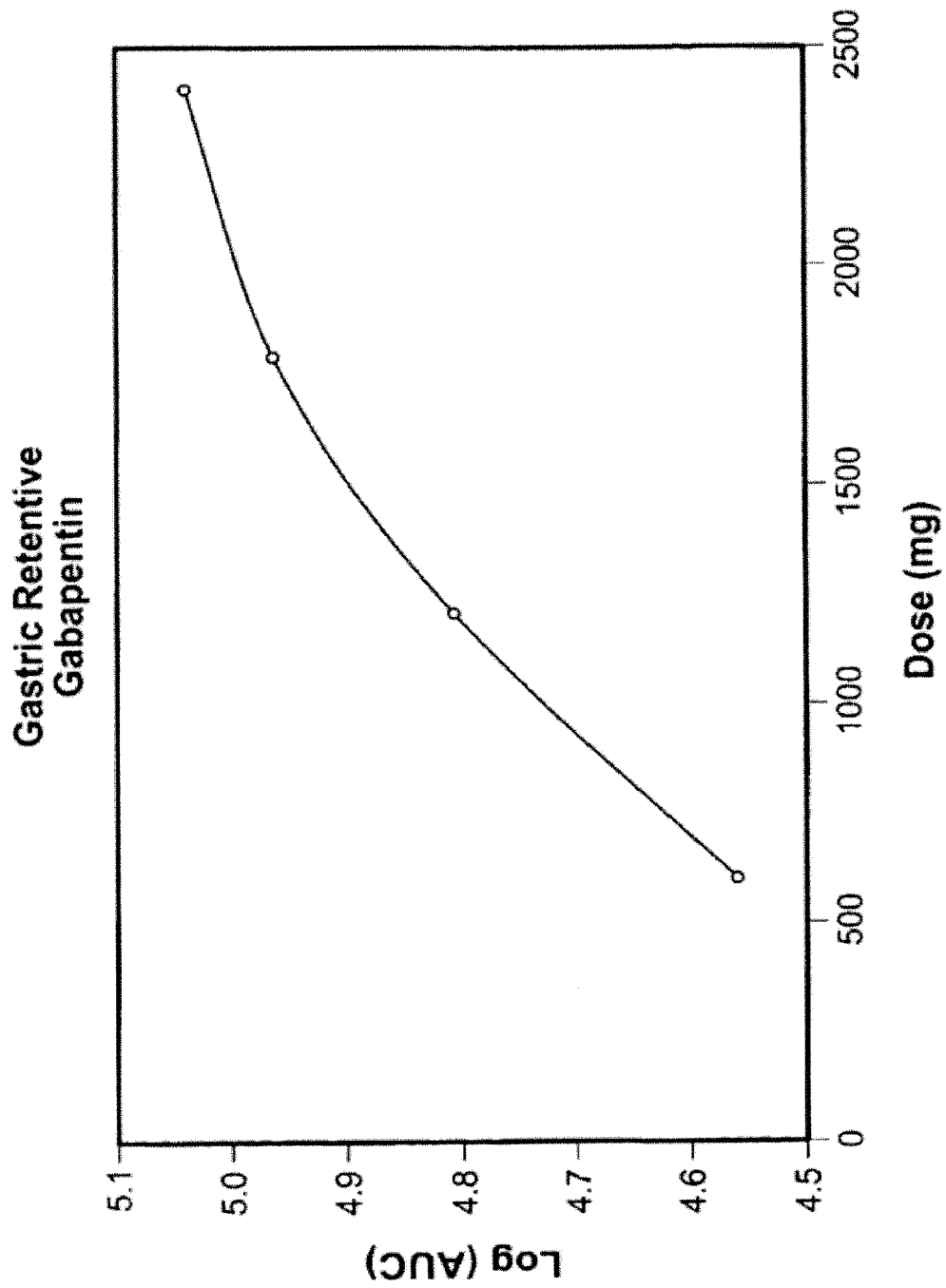

The term "AUC" (i.e., "area under the curve," "area under the concentration curve," or "area under the concentration-time curve") is a pharmacokinetic term used to refer a method of measurement of bioavailability or extent of absorption of a drug based on a plot of an individual or pool of individual's blood plasma concentrations sampled at frequent intervals; the AUC is directly proportional to the total amount of unaltered drug in the patient's blood plasma. For example, a linear curve for a plot of the AUC versus dose (i.e., straight ascending line) indicates that the drug is being released slowly into the blood stream and is providing a steady amount of drug to the patient; if the AUC versus dose is a linear relationship this generally represents optimal delivery of the drug into the patient's blood stream. By contrast, a non-linear AUC versus dose curve indicates rapid release of drug such that some of the drug is not absorbed, or the drug is metabolized before entering the blood stream. Within the context of the present invention, FIGS. 3-6 show the difference between the AUC as a function of dose for immediate release gabapentin (NEU-RONTIN®) (FIGS. 3 and 5) versus the AUC as a function of dose for the gastric retentive gabapentin of the present invention (FIGS. 4 and 6). The data from Table 6 and FIG. 2 indicates that gastric retentive gabapentin has an AUC that is approximately equivalent to comparable doses of immediate release gabapentin while the graphs set forth at FIGS. 3-6 indicate that gastric retentive gabapentin may actually have greater bioavailability than comparable doses of immediate release gabapentin.

The term "$C_{max}$" (i.e., "maximum concentration") is a pharmacokinetic term used to indicate the peak concentration of a particular drug in the blood plasma of a patient. Within the context of the present invention, for immediate release formulations of gabapentin, the $C_{max}$ is generally higher than the $C_{max}$ of gastric retentive gabapentin because the latter releases the drug more slowly than the former and thus, the gastric retentive gabapentin at the same dose does not achieve a peak concentration as high as the comparable dose of immediate release gabapentin. As shown in FIG. 2, and Table 6 of Example 4, the $C_{max}$ of gastric retentive gabapentin (600 mg) is approximately 30% to approximately 50% less than the $C_{max}$ for a comparable dose of immediate release gabapentin.

The term "$T_{max}$" (i.e., "time of maximum concentration" or "time of $C_{max}$") is a pharmacokinetic term used to indicate the time at which the $C_{max}$ is observed during the time course of a drug administration. Within the context of the present invention, $T_{max}$ is also longer for gastric retentive gabapentin when compared to immediate release gabapentin. As shown in FIG. 2 and Table 6 of Example 4, the $T_{max}$ for gastric retentive gabapentin (600 mg) is approximately 1.5 to approximately 3.5 hours longer (equivalent to approximately 40% to approximately 80% slower) than the $T_{max}$ for a comparable dose of immediate release gabapentin. As would be expected, a dosage form that would include an immediate release as well as a gastric retentive component would have a $T_{max}$ that is higher than the $T_{max}$ for an immediate release dosage form, but lower than the $T_{max}$ for a purely gastric retentive dosage form.

The term "half-life" is a pharmacokinetic term used to indicate the length of time necessary to eliminate 50% of the remaining amount of drug present in the body.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. The term "pharmacologically active" (or simply "active") as in a "pharmacologically active" derivative, refers to a derivative having the same type of pharmacological activity as the parent compound and approximately equivalent in degree. When the term "pharmaceutically acceptable" is used to refer to a derivative (e.g., a salt) of an active agent, it is to be understood that the compound is pharmacologically active as well. When the term, "pharmaceutically acceptable" is used to refer to an excipient, it implies that the excipient has met the required standards of toxicological and manufacturing testing or that it is on the Inactive Ingredient Guide prepared by the FDA, or comparable agency.

The term "soluble" as used herein refers to a drug having an aqueous solubility (measured in water at 20° C.) greater than 10%, preferably greater than 20%, by weight. The terms "slightly soluble" and "sparingly soluble" refer to a drug having an aqueous solubility (measured at 20° C.) in the range of 2% to 10% by weight, while drugs having an aqueous solubility in the range of 0.001% to less than 2% by weight are referred to as "substantially insoluble."

The terms "hydrophilic" and "hydrophobic" are generally defined in terms of a partition coefficient P, which is the ratio of the equilibrium concentration of a compound in an organic phase to that in an aqueous phase. A hydrophilic compound has a P value less than 1.0, typically less than about 0.5, where P is the partition coefficient of the compound between octanol and water, while hydrophobic compounds will generally have a P greater than about 1.0, typically greater than about 5.0. The polymeric carriers herein are hydrophilic, and thus compatible with aqueous fluids such as those present in the human body.

The term "polymer" as used herein refers to a molecule containing a plurality of covalently attached monomer units, and includes branched, dendrimeric, and star polymers as well as linear polymers. The term also includes both homopolymers and copolymers, e.g., random copolymers, block copolymers and graft copolymers, as well as uncrosslinked polymers and slightly to moderately to substantially crosslinked polymers, as well as two or more interpenetrating cross-linked networks.

The term "vesicle" as used herein refers to a small (e.g., 0.01 to 1.0 mm), usually spherical structure that may contain or be composed of either lipoidal or aqueous material, or both. Suitable vesicles include, but are not limited to, liposomes, nanoparticles, and microspheres composed of amino acids. While vesicles are usually membrane-bound, they need not necessarily be membrane bound and within the context of the present invention, the term "vesicle" includes both membrane-bound and non-membrane-bound structures.

The terms "swellable" and "bioerodible" (or simply "erodible") are used to refer to the polymers used in the present dosage forms, with "swellable" polymers being those that are capable of absorbing water and physically swelling as a result, with the extent to which a polymer can swell being determined by the molecular weight or degree of crosslinking (for crosslinked polymers), and "bioerodible" or "erodible" polymers referring to polymers that slowly dissolve and/or gradually hydrolyze in an aqueous fluid, and/or that physically disentangle or undergo chemical degradation of the chains themselves, as a result of movement within the stomach or GI tract.

The in vivo "release rate" and in vivo "release profile" refer to the time it takes for the orally administered dosage form, or the active agent-containing layer of a bilayer or multilayer tablet (administered when the stomach is in the fed mode) or the content of the active ingredient to be reduced to 0-10%, preferably 0-5%, of its original size or level, as may be observed visually using NMR shift reagents or paramagnetic species, radio-opaque species or markers, or radiolabels, or determined mathematically, such as deconvolution, upon its plasma concentration profiles.

The term "fed mode," as used herein, refers to a state which is typically induced in a patient by the presence of food in the stomach, the food-giving rise to two signals, one that is said to stem from stomach distension and the other a chemical signal based on food in the stomach. It has been determined that once the fed mode has been induced, larger particles are retained in the stomach for a longer period of time than smaller particles; thus, the fed mode is typically induced in a patient by the presence of food in the stomach.

In the normal digestive process, the passage of matter through the stomach is delayed by a physiological condition that is variously referred to as the digestive mode, the postprandial mode, or the "fed mode." Between fed modes, the stomach is in the interdigestive or "fasting" mode. The difference between the two modes lies in the pattern of gastroduodenal motor activity.

In the fasting mode, the stomach exhibits a cyclic activity called the "interdigestive migrating motor complex" or "IMMC". This activity occurs in four phases:

Phase I, which lasts 45 to 60 minutes, is the most quiescent, with the stomach experiencing few or no contractions;

Phase II, characterized by sweeping contractions occurring in an irregular intermittent pattern and gradually increasing in magnitude;

Phase III, consisting of intense bursts of peristaltic waves in both the stomach and the small bowel, lasting for about 5 to 15 minutes; and Phase IV is a transition period of decreasing activity which lasts until the next cycle begins.

The total cycle time for all four phases is approximately 90 minutes. The greatest activity occurs in Phase III, when powerful peristaltic waves sweep the swallowed saliva, gastric secretions, food particles, and particulate debris, out of the stomach and into the small intestine and colon. Phase III thus serves as an intestinal housekeeper, preparing the upper tract for the next meal and preventing bacterial overgrowth.

The fed mode is initiated by nutritive materials entering the stomach upon the ingestion of food. Initiation is accompanied by a rapid and profound change in the motor pattern of the upper GI tract, over a period of 30 seconds to one minute. The change is observed almost simultaneously at all sites along the G.I. tract and occurs before the stomach contents have reached the distal small intestine. Once the fed mode is established, the stomach generates 3-4 continuous and regular contractions per minute, similar to those of the fasting mode but with about half the amplitude. The pylorus is partially open, causing a sieving effect in which liquids and small particles flow continuously from the stomach into the intestine while indigestible particles greater in size than the pyloric opening are retropelled and retained in the stomach. This sieving effect thus causes the stomach to retain particles exceeding about 1 cm in size for approximately 4 to 6 hours.

Within the context of the present invention, the term "pain" as used herein refers to a pain state experienced by a human individual or a mammal (also referred to as a "patient" herein) that includes a non-nociceptive pain, i.e., a neuropathic pain, a sympathetic pain, or both. As used herein, the term "pain" is also intended to include a mixed pain syndrome that includes a nociceptive pain state in addition to a non-nociceptive pain state. Examples of neuropathic pain include, without limitation, diabetic neuropathy, HIV sensory neuropathy, post-herpetic (or post-shingles) neuralgia, post-thoracotomy pain, trigeminal neuralgia, radiculopathy, neuropathic pain associated with chemotherapy, reflex sympathetic dystrophy or causalgia also known as nerve damage (for example carpal tunnel syndrome), back pain, peripheral neuropathy (known as widespread nerve damage experienced in the limbs and regions extending from the central nervous system), entrapment neuropathy (e.g., carpel tunnel syndrome), phantom limb pain, and complex regional pain syndrome. As previously noted, sympathetic pain occurs most commonly after fractures and soft tissue injuries of the arms and legs. Because pain is difficult to define and characterize, it is to be understood that a patient being treated for a particular non-nociceptive pain state, such as the neuropathic pain condition of neuralgia, may also be experiencing a sympathetic pain condition or a nociceptive pain condition. In this respect, the term "pain" as used herein is used to include a mixed syndrome pain that includes mixed syndrome non-nociceptive pain (i.e., pain that includes both neuropathic and sympathetic pain) or a nociceptive pain that accompanies a non-nociceptive pain state. Examples of mixed syndrome non-nociceptive pain are pain associated with post-menopausal symptoms, or pain associated with chronic pelvic pain syndrome. A migraine headache is considered to be one example of a mixed syndrome pain state that is a mixture of neuropathic and somatic (i.e., nociceptive) pain.

With respect to pain, the terms "treating" and "treatment" as used herein refer to reduction in severity and/or frequency of pain symptoms, elimination of pain symptoms and/or the underlying cause for pain symptoms and the improvement or remediation of damage caused by the pain symptoms. With respect to other conditions or diseases, the terms "treating" and "treatment" includes the following actions inhibiting the disease, i.e., arresting its development; or relieving the disease, i.e., causing regression of the disease.

Prevention includes delaying or inhibiting the occurrence of pain symptoms and/or their underlying cause, e.g., delaying or inhibiting the disease from occurring in a subject which may be predisposed to the disease, but has not yet been diagnosed as having it.

Active Agents

Active agents that may be used with the dosage forms of the present invention include the GABA analog gabapentin and the related GABA analog pregabalin (S)-(3-aminomethyl)-5-methylhexoanoic acid) or (S)-isobutyl GABA. In addition to gabapentin and pregabalin, it is contemplated that other GABA analogs may be used as active agents in the manufacture of the dosage forms and the methods described herein. Examples of other GABA analogs that may be used within the context of the present invention include, without limitation, cis-(I-S,3R)-(1-aminomethyl)-3-methylcyclohexane)acetic acid; 1a,3a,5a-(1-aminomethyl)-(3,5-dimethylcyclohexane) acetic acid; (9-(aminomethyl)bicyclo[3.3.1]non-9-yl)acetic acid; and (7-(aminomethyl)bicycle[2.2.1]hept-7-yl)acetic acid. Bryans et al. J MED CHEM 41:1838-1845 (1998); Bryans et al., MED RES REV 19:149-177 (1999).

Within the context of the present invention, the GABA analogs are preferably used in free amphoteric form, including zwitterionic form; however, pharmaceutically acceptable salt forms, hydrates or solvates that retain the biological effectiveness and properties of gabapentin, pregabalin, and/or other GABA analogs are not biologically or otherwise undesirable, can also be used and may show superior bioavailability. In this respect, as used herein, the terms "gabapentin" and "pregabalin" and "GABA analogs" are intended to include the agent itself, as well as its pharmaceutically acceptable salts.

Pharmaceutically acceptable salts may be amphoteric and may be present in the form of internal salts. In this respect, the gabapentin, pregabalin, and other GABA analogs described herein may form acid addition salts and salts with bases. Exemplary acids that can be used to form such salts include, by way of example and not limitation, mineral acids such as hydrochloric, hydrobromic, sulfuric or phosphoric acid or organic acids such as organic sulfonic acids and organic carboxylic acids. Salts formed with inorganic bases include, for example, the sodium, potassium, lithium, ammonium, calcium, and magnesium salts. Salts derived from organic bases include, for example, the salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethyl aminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, fumarate, maleate, succinate, acetate and oxalate. The invention also contemplates administering one or more additional therapeutic agents with the gabapentin treatment. The selection of these additional therapeutic agents will depend upon the specific disease state or condition that is being treated.

Additional therapeutic agents that can be used with the gastric retentive gabapentin of the present invention to treat any of the various pain states described above, include anticonvulsants, tricyclic antidepressants, opioids, and secondary analgesics. Examples of suitable anticonvulsants include carbamazepine, phenyloin, and lamotrigine. Examples of suitable tricyclic antidepressants include amitriptyline, imipramine, clomipramine, and desipramine. Examples of suitable opioids include oxycodone and tramadol.

For those embodiments of the invention where the gabapentin gastric retentive dosage form is administered for prophylactic treatment of migraine headaches, such additional therapeutic agents can be selected from the group consisting of tricyclic antidepressants (amitriptyline, doxepin, imipramine, maprotiline, protriptyline, desipramine), SSRI (fluoxetine), triptine (sumatriptan, etc.), and ergotamine.

Where the additional therapeutic agent is a secondary analgesic, any analgesic that would complement the treatment protocol of the gastric retentive gabapentin of the present invention can be administered with gabapentin, either at the same time or at different times in order to treat the pain condition at hand. The secondary analgesic would typically be administered at least once in a 24-hour period, and can be any analgesic effective for treatment of pain. One type of analgesic that may be used in conjunction with the gastric retentive gabapentin of the present invention is non-steroidal anti-inflammatory drugs ("NSAIDs").

Dosing Regimens and Pharmacokinetics

Generally, the frequency of administration of a particular dosage form is determined to provide the most effective results in an efficient manner without overdosing and varies according to the characteristics of the particular drug, including both its pharmacological characteristics and its physical characteristics, such as solubility. In some embodiments, the characteristics of the swellable matrix, such as its permeability, and the relative amounts of the drug and polymer will also affect frequency of administration. In most cases, the dosage form is prepared such that effective results are achieved with administration once every eight hours, once every twelve hours, or once every twenty-four hours. As previously discussed, due to the physical constraints placed on a tablet or capsule that is to be swallowed by a patient, most dosage forms can only support a limited amount of drug within a single dosage unit.

In one embodiment, the present invention relates to a method of treating a pain state, by administering a therapeutically effective amount of gabapentin, or a pharmaceutically acceptable salt thereof, to a patient in need of such treatment in a gastric retentive dosage form that is administered to the patient in a once-daily or twice-daily dosing regimen. The method of the present invention is useful for treating numerous pain states that are currently being treated with conventional immediate release formulations of gabapentin and include, by way of illustration and not limitation, pain states exhibiting neuropathic pain, sympathetic pain, a mixture of neuropathic pain and sympathetic pain, or a mixture of neuropathic pain or sympathetic pain with nociceptive pain.

Within the context of the present invention, the gastric retentive gabapentin of the present invention has the advantage of improving patient compliance with gabapentin administration protocols because the drug is administered in a once-daily or twice-daily dosing regimen, rather than the multiple dosing administrations necessary for the immediate release dosage forms of gabapentin. For one embodiment of the present invention, when administered in the fed mode, the gastric retentive gabapentin dosage forms are retained for a period of time in the stomach and the release of the drug is extended beyond the release time of an immediate release dosage form. One embodiment of the invention relates to a method of administering a therapeutically effective amount of gabapentin to a patient in need thereof, comprising administering gabapentin or pharmaceutically acceptable salt thereof, in a gastric retentive dosage form once in the morning or evening in a once a day daily dosing regimen. Another embodiment comprises administering a therapeutically effective amount of gabapentin to a patient in need thereof, comprising administering gabapentin or a pharmaceutically acceptable salt thereof, in a gastric retentive dosage form twice a day, for example once in the morning and once in the evening in a twice a day daily dosing regimen.

In addition to the foregoing, one embodiment of the gastric retentive dosage forms of the present invention can lower the maximum plasma concentration of the drug in a patient's blood when compared to a similar dose of immediate release (IR) gabapentin thereby reducing any side effects from the drug. The following discussion references gabapentin for purposes of illustration and not for purposes of limiting the dosage forms of the present invention solely to gabapentin; in this respect, pregabalin and other GABA analogs are expected to behave similarly to gabapentin.

Since gabapentin is absorbed high in the GI (gastrointestinal) tract by means of a saturable transport mechanism, a gastric retentive dosage form is particularly beneficial for delivery of gabapentin since the dosage form can keep the drug in the region of absorption for an extended period of time and consequently improve bioavailability of the drug. By virtue of the slower release rate of the gastric retentive gabapentin of the present invention, saturation of the carrier-mediated transport of conventional dosages is avoided. The gastric retentive dosage form of the present invention is particularly beneficial for delivery of gabapentin due to its prolonged transit in the upper GI tract, which allows the drug to be absorbed adequately in the preferred region of absorption. Further, as shown in AG. 2, the gastric retentive gabapentin dosage forms of the present invention increase the $T_{max}$ for the drug and lower the $C_{max}$ for the drug, which may result in reduced incidence and/or severity of the central nervous system (CNS) side effects of the drug, such as somnolence, dizziness, fatigue, ataxia, weight gain, peripheral edema, diarrhea, headache, dry mouth, blurred vision, and/or reversible visual field constriction.

In one embodiment of the present invention, the gastric retentive gabapentin is administered in a once-daily dosing regimen with a total daily dose of gabapentin ranging from about 300 mg/day to about 9600 mg/day, depending on the disease state or condition that is being treated.

In another embodiment of the invention, the gastric retentive gabapentin is administered in the morning and evening in a twice a day daily dosing regimen with a total daily dose of gabapentin ranging from about 300 mg/day to about 9600 mg/day.

Where the total daily dose of gabapentin is 1000 mg or greater, the patient is preferably titrated up to the maximum maintenance dose that the patient is capable of tolerating. Titration is preferable with both the once-daily and twice-daily dosing regimens.

With the twice-daily dosing regimen, the two dosings may be administered in a symmetric or asymmetric dosing regimen. With a symmetric dosing regimen, the morning dose is the same as the evening dose. Thus, a symmetric dosing regimen may consist of 300 mg of gabapentin in the morning and 300 mg of gabapentin in the evening for a total daily dose of 600 mg of gabapentin for a single 24 hour period. With gabapentin, symmetric dosing regimens are best used where lower dosages of gabapentin are being used for treating a particular disease state or condition. With the twice-daily dosing regimen in an asymmetric dosing regimen, the morning and evening doses will not be the same. Where high doses of gabapentin are being used to treat a particular disease state or condition, asymmetric dosing regimens are preferred. Examples of asymmetric dosing regimens can be, for example, 300 mg in the morning and 1200 mg in the evening for a total daily dose of 1500 mg/day; 600 mg in the morning and 3600 mg in the evening for a total daily dose of 4200 mg/day; or 900 mg in the morning and 6000 mg in the evening for a total daily dose of 6900 mg/day. Differential dosing levels may also be used for a dosing regimen, such as for example, where different dosages are administered for the morning and evening doses during the asymmetric treatment course. Under this scenario, a patient may have a decreasing morning dose and an increasing evening dose, or an increasing morning dose and a decreasing evening dose during a particular part of the dosing regimen.

Individual dosage units for both the once-daily and twice-daily dosing regimens will generally contain from about 100 mg to about 1800 mg of gabapentin per dosage unit. Presently, any dosing regimen for the gastric retentive gabapentin of the present invention must take into consideration both the amount of the gabapentin in a single dosage unit and the number of tablets or capsules that can be consumed together to reach the desired daily dose and/or maintenance dose. For example, for a dosing regimen comprised of a once-daily dosing of 1800 mg of gastric retentive gabapentin, three 600 mg tablets or a 1200 mg tablet or capsule may be taken together with a 600 mg tablet at the evening meal. If the patient finds that the 1200 mg tablet is too large, then the patient may take two 600 mg tablets or three 400 mg tablets. For a dosing regimen comprised of a twice-daily dosing of 1800 mg of gastric retentive gabapentin, 600 mg may be taken with a morning meal and 1200 mg (in one or multiple dosage units) may be taken with an evening meal.

For all modes of administration, for the embodiment of the present invention for which the gastric retentive dosage is a swellable matrix which relies upon dosing in the fed mode to increase the gastric residence time, the gastric retentive gabapentin dosage forms are preferably administered in the fed mode, i.e., with or just after consumption of a meal. Because two of the side effects of gabapentin are somnolence and dizziness, it is preferable, when possible, for the patient to take the once-daily dose or the larger of the twice-daily doses with an evening meal. In this way, the patient may avoid the side effects by sleeping through the side effects, thus permitting better compliance and optimization of the dosing regimen. When administered in the evening fed mode, one embodiment of the gastric retentive gabapentin of the present invention will provide the patient with continued relief from the particular disease state or condition under treatment through the night and into the next day. The gastric retentive gabapentin dosage form of the present invention is able to provide relief from the disease state or condition under treatment for an extended period of time because the dosage form allows for both extended release of the gabapentin and the superior absorption of the drug in the GI tract.

As previously discussed, with both the once-daily and twice-daily dosing regimens described herein, the total daily dose of gabapentin may be titrated up to a maximum amount per day, also called the maintenance dose. The length of time for the titration process will vary with the individual patients, but will generally range from approximately two days to approximately two weeks. Likewise, where a patient is nearing the completion of a therapeutic course of gabapentin, the patient may be weaned off the maintenance dose over a period of days or weeks so that the patient's body has a chance to adjust to the reduction of medication slowly.

That the gastric retentive gabapentin dosage form of the present invention may be administered in once-daily or twice-daily dosing regimens as described herein is particularly surprising and unexpected when compared to the behavior of immediate release gabapentin. Specifically, immediate release gabapentin is not well absorbed in the colon and has such a short half-life that it must be administered at least three times a day in order to achieve a desired level of pain relief. Non gastric-retentive extended release gabapentin formulations may deliver a significant fraction of the drug to the lower GI tract, and therefore the drug is not well absorbed, thereby decreasing bioavailability of the drug when compared to the bioavailability of an equivalent immediate release dose. Thus, gastric retentive dosage forms of gabapentin allow for extended delivery of gabapentin without significant loss of bioavailability. However, the slower absorption of the gastric retentive gabapentin of the present invention allows for administration of the drug in a once or twice daily dosing regimen with improved pain relief and without exacerbation of the incidence of adverse side effects. FIG. 2 and Table 6 of Example 4 provide evidence of the slower release of gabapentin as compared to immediate release gabapentin into the bloodstream through measurements. The data in Tables 6 indicates that gastric retentive gabapentin has a $C_{max}$ that is approximately 30% to approximately 50% less than the $C_{max}$ of a comparable dose of immediate release gabapentin.

In addition to a decrease in $C_{max}$, the gastric retentive dosage forms of the present invention also show increased $T_{max}$ (FIG. 2 and Table 6 of Example 4) providing further evidence for the longer lasting effects of the gastric retentive gabapentin of the present invention when compared to immediate release gabapentin. The data in Table 6 indicates that 600 mg of gastric retentive gabapentin has a $T_{max}$ that is approximately 1.5 to approximately 3.5 hours longer (equivalent to approximately 40% to approximately 80% slower) than the $T_{max}$ of a comparable dose of immediate release gabapentin.

A further surprising and unexpected feature of the gastric retentive gabapentin dosage forms of the present invention is that the gastric retentive dosage forms enable greater bioavailability of the higher doses of gabapentin when compared to a comparable dose of immediate release gabapentin. Specifically, according to the Summary Basis of Approval for NEUROTNIN® (New Drug Application ("NDA") 20-235), the normalized AUC(600-mg) of 600-mg, 800-mg, 1200 mg and 1600-mg in four subjects were 53%, 37%, 38% and 29%, respectively where the AUC was obtained at steady-state. For one embodiment of the present invention, the $AUC_{0-\infty}$ (ng*hr/ml) (geometric mean of 19 subjects) values for escalating doses of 600-mg, 1200-mg, 1800-mg and 2400-mg administered as single-doses immediately after a meal to healthy volunteers were 35698, 63209, 90894, and 108572, respectively (rounded to the nearest whole number). Because the $AUC_{0-\infty}$ for a single dose is equivalent to the steady-state AUC as measured between dosing intervals, the AUC values in both cases represent the $AUC_{0-\infty}$ and comparisons can be made. Therefore, if a ratio of the AUC to that obtained at 600-mg dose, and normalized for the dose administered is made, the ratios for the NEUROTNIN© capsules are 1.0, 0.698, 0.717 and 0.547 for the 600-mg, 800-mg, 1200 mg and 1600-mg respectively compared to ratios for one embodiment of the present invention of 1.0, 0.882, 0.843 and 0.753 for the 600-mg, 1200-mg, 1800-mg and 2400-mg doses, respectively. Thus, the fraction of the dose that is absorbed decreases by about 50% when the dose is increased from 600-mg to 1600 mg for NEURONTIN® capsules. In contrast, for one embodiment of the present invention, the fraction of the dose that is absorbed decreases by about 25% when the dose is increased from 600 mg to 2400 mg, and only 15% at 1800 mg, which is still above the 1600 mg dose of immediate release NEURONTIN® which demonstrated a loss of almost 50% compared to the 600-mg dose of immediate release NEURONTIN®. FIGS. 3-6 provide evidence of the enhanced bioavailability of the gastric retentive gabapentin of the present invention as compared to immediate release gabapentin through AUC measurements. In addition, Example 12 demonstrates comparable AUC over 24 hours for the twice-daily gabapentin as compared to three times daily NEURONTIN® at the same total daily dose of 1800 mg.

Further, as gabapentin is known to exhibit saturable absorption (i.e., where a drug is absorbed only to the amount of saturation), it is also surprising and unexpected that the gastric retentive gabapentin dosage forms of the present invention are capable of being administered in doses that are two to six times the doses administered for immediate release gabapentin while retaining sufficient bioavailability to attain the therapeutic effects of the conventional immediate release gabapentin dosage forms. As shown in FIGS. 4 and 6, the slower absorption of the gastric retentive gabapentin of the present invention permits nearly linear absorption over the range of 600 mg to 2400 mg of gastric retentive gabapentin administered at one dosing. FIGS. 3 and 5 show that immediate release gabapentin NEURONTIN®) is saturated at 1200 mg and thus, is unavailable to deliver additional drug to the patient at dosages above 1200 mg (although not all 1200 mg is absorbed for either case). The saturable absorption mechanism may also explain the higher loss of bioavailability observed in the NDA for the NEURONTIN® when compared to the present invention.

A particularly beneficial advantage of the once or twice daily dosing regimens for the gastric retentive gabapentin of the present invention is that when the once-daily dosing is administered in the evening, or when the larger of the twice-daily dosing is administered in the evening, the patient is able to experience the therapeutic effects of gabapentin throughout the night. As a result of the linear absorption of the drug in the gastric retentive dosage forms of the present invention, the gabapentin is released continuously throughout the night thus providing continuous therapy. Tables 9-12 of Example 10 shows data obtained from a clinical trial conducted with the gastric retentive gabapentin dosage form of the present invention where the gabapentin was administered in once daily and twice daily dosing regimens. In addition, Example 12 demonstrates data obtained from a clinical trial conducted with the gastric retentive gabapentin dosage form of the present invention where the gabapentin was administered in once daily and twice daily dosing regimens.

Another beneficial advantage of the gastric retentive gabapentin of the present invention is that when it is administered at a sufficiently high dose with an evening meal, the somnolence and/or dizziness, typically associated with higher dosages of gabapentin administered in other ways, are ameliorated with nighttime sleep. Another advantage of administering a high evening dose of gastric retentive gabapentin is that the dosage form will allow for continued therapy upon waking and potentially throughout the next day until the next evening administration. Where appropriate if necessary, a small morning dosing (e.g., 300 mg) may be administered to supplement the larger evening dosages. There is also an advantage of the reduced gastric motility at night time over that in the day time (induced by the fed mode) which has to be maintained for an extended period of time (with meals).

Another advantage of the present invention is that it may allow patients who are unable to reach an effective therapeutic dose of gabapentin to be effectively treated with gabapentin. For those patients who are unable to reach an effective dose of gabapentin due to inability to tolerate side effects, the combination of extended release with a lower maximum concentration ($C_{max}$) compared to the equivalent IR dose if both are administered as single doses, as well as the dosing regimen in which all or a larger fraction of the dose, is administered after the evening meal, may lower the incidence of side effects sufficiently to allow the patient to reach a therapeutically effective dose. Moreover, some patients may not be effectively treated with gabapentin because they experience no increase in efficacy with increased dose. The present invention will allow for a larger percentage of the administered dose to be absorbed at higher doses when compared to immediate release gabapentin, and thus may allow some patients to obtain efficacious treatment who found immediate release gabapentin insufficient. Thus, the combination of dosing regimen, increased bioavailability (when compared to immediate release gabapentin) and the extended release of gabapentin over time may allow for reduced incidence of side effects and as a result, improved efficacy as more patients may be able to reach an efficacious dose.

As previously noted, the patient may be titrated up to the maintenance dose (i.e., the highest maximum dose allowable or preferred for a patient). Titration may occur over a period of days or weeks, depending on the patient's therapeutic needs, the magnitude of the maintenance dose, and the patient's apparent tolerance for gabapentin. Titration will generally be determined by the administrating practitioner.

Likewise the patient may be weaned from the high maintenance dose down to a zero dose in a gradual process that allows the patient's body to adjust to reduced medication and to determine whether the gabapentin therapy is sufficient at the lower dose.

When the administration of an additional therapeutic agent in addition to the gabapentin is desired, the additional active agent may be administered at the same time or at a different time than gabapentin. For purposes of facilitating patient compliance, administration of any of the aforementioned additional agents at the same time is preferred.

Dosage Forms

There are several drug delivery systems that are suitable for use in delivering gabapentin in the method of the invention as they are particularly tailored to be gastric-retentive dosages, such as the swellable bilayer described in U.S. Pat. No. 5,232,704 to Franz et al.; the multilayer tablet with a band described in U.S. Pat. No. 6,120,803 to Wong et al.; the membrane sac and gas generating agent described in U.S. Pat. No. 4,996,058 to Sinnreich; the swellable, hydrophilic polymer system described in U.S. Pat. No. 5,972,389 to Shell et al. and WO 98/55107 to Shell et al.; all of which are incorporated herein by reference.

Of particular interest are gastric retentive dosage forms that contain hydrophilic polymers that swell to a size such that the dosage form is retained in the fed mode. For example, the gastric retentive dosage form can contain polymers with a high swelling capacity such as polyethylene oxide, hydroxyethylcellulose, and hydroxypropylmethylcellulose. The polymers are preferably of a moderate to high molecular weight ($4 \times 10^3$ to greater that $10^7$) to enhance swelling and provide control of the release of gabapentin. In one embodiment of the invention, a hydroxypropylmethylcellulose polymer of such molecular weight is utilized so that the viscosity of a 1% aqueous solution is about 4000 cps to greater than 100,000 cps. An example of suitable polyethylene oxide polymers are those having molecular weights (viscosity average) on the order of 2-7 million. A typical dosage form should swell to approximately 115% of its original volume within one hour after administration, and at a later time should swell to a volume that is 130% or more of the original volume. Fillers, binders, lubricants and other additives may also be included in the gastric retentive dosage form, such as are well known to those of skill in the art.

The gastric retentive dosage forms of the present invention provide for a drug delivery profile such that gabapentin, both on an in vivo and in vitro basis, is delivered for at least 5 hours and more typically over a time period of about 8-10 hours. In order to provide for sustained delivery, it is preferable that at least 40 wt % of gabapentin is retained in the dosage form after 1 hour, i.e., no more than 60 wt % of the drug is administered in the first hour. In addition, it may be desired to utilize a dosage form that provides for substantially all of the gabapentin to be delivered over the intended duration, which is typically about 6-12 hours, where substantially all is taken to mean at least about 85 (generally the art teaches that substantially all is 80 wt %) of the gabapentin is administered.

The gastric retentive gabapentin forms of the present invention can be made by techniques that are well established in the art, including wet granulation, fluid-bed granulation, dry granulation, direct compression, and so forth.

In one embodiment of the invention, the gabapentin dosage forms contain one or more hydrophilic polymers that swell unrestrained dimensionally to a size such that the dosage form is retained in the fed mode. The polymers are preferably of a moderate to high molecular weight ($4 \times 10^3$ to greater that $10^7$) to enhance swelling and provide control of the release of gabapentin. A typical dosage form should swell to approximately 115% of its original volume within one hour after administration, and at a later time should swell to a volume that is 130% or more of the original volume. The molecular weight of the polymer may be selected based upon viscosity of the polymer in solution. For example, the polymer may be selected such that a 1% aqueous solution has a viscosity in a range of 4000 cps (centipoise) to greater than 100,000 cps. Examples of such polymers include, by way of illustration and not limitation, polymers with a high swelling capacity such as polyethylene oxide ("PEO"), hydroxyethylcellulose, and hydroxypropylmethylcellulose ("HPMC" also known as hypromellose). Examples of suitable PEO polymers are those having molecular weights (viscosity average) on the order of 2-7 million.

In another embodiment of the present invention, there is provided a gastric retentive swellable, sustained-release dosage form having a matrix comprised of PEO and HPMC that releases gabapentin to the upper GI tract. The dosage form may be a single-layer or a bilayer tablet. Where the dosage form is a bilayer tablet, one layer is the active agent containing layer that releases the gabapentin while the other layer is a swelling or floating layer. Further details on the formulation of gastric retentive swellable, sustained-release may be found in commonly owned U.S. Pat. No. 6,723,340 Gusler et al., which is incorporated herein by reference. Examples 1, 2, and 3 describe the formulation of gastric retentive swellable gabapentin forms made by dry granulation with PEO and HPMC.

A typical dosage form would provide for a drug delivery profile such that gabapentin both on an in vivo and in vitro basis is delivered for at least 5 hours, and typically over a time period of about 8-10 hours. In order to provide for sustained delivery, it is preferable that at least 40 wt % of gabapentin is retained in the dosage form after 1 hour, i.e., no more than 60 wt % of the drug is administered in the first hour. In addition, it may be desired to utilize a dosage form that provides for substantially all of the gabapentin to be delivered over the intended duration, which is typically about 6-12 hours, where substantially all is taken to mean at least about 85 (generally the art teaches that substantially all is 80) wt % of the gabapentin is administered.

In one embodiment of the invention, the gastric retentive dosage form of gabapentin is a capsule dosage form that allows for the extended release of gabapentin in the stomach and comprises: (a) at least one component that expands on contact with gastric juice and contains an agent capable of releasing carbon dioxide or nitrogen, and gabapentin or a pharmaceutically acceptable salt thereof; (b) at least one hydrophilic membrane in the form of a sachet which contains component (a), expands by inflation, floats on the aqueous phase in the stomach and is permeable to gastric juice and; (c) capsule dosage form which contains components (a) and (b) and which disintegrates without delay in the stomach under the action of gastric juice. Component (a) may also contain a pharmaceutically acceptable hydrophilic swelling agent such as lower alkyl ethers of cellulose, starches, water-soluble aliphatic or cyclic poly-N-vinylamides, polyvinyl alcohols, polyacrylates, polymethacrylates, polyethylene glycols and mixtures thereof, as well as other materials used in the manufacture of pharmaceutical dosage forms. Further details regarding an example of this type of dosage form can be found in U.S. Pat. No. 4,996,058 to Sinnreich.

In another embodiment of the invention, the gastric retentive dosage form of gabapentin is an extended release oral drug dosage form for releasing gabapentin into the stomach, duodenum and small intestine of a patient, and comprises: a single or a plurality of solid particles consisting of gabapentin or a pharmaceutically acceptable salt thereof dispersed within a polymer that (i) swells unrestrained dimensionally by imbibing water from gastric fluid to increase the size of the particles to promote gastric retention in the stomach of the patient in which the fed mode has been induced; (ii) gradually the gabapentin diffuses or the polymer erodes over a time period of hours, where the diffusion or erosion commences upon contact with the gastric fluid; and (iii) releases gabapentin to the stomach, duodenum and small intestine of the patient, as a result of the diffusion or polymeric erosion at a rate corresponding to the time period. Exemplary polymers include polyethylene oxides, alkyl substituted cellulose materials and combinations thereof, for example, high molecular weight polyethylene oxides and high molecular weight or viscosity hydroxypropylmethylcellulose materials. Further details regarding an example of this type of dosage form can be found in U.S. Pat. No. 5,972,389 to Shell et al. and WO 9855107 to Shell et al.

In yet another embodiment, a bi-layer tablet releases gabapentin to the upper GI tract from an active containing layer, while the other layer is a swelling or floating layer. Details of this dosage may be found in U.S. Pat. No. 5,232,704 to Franz et al. This dosage form may be surrounded by a band of insoluble material as described in U.S. Pat. No. 6,120,803 to Wong et al.

Another embodiment of the invention uses a gastric retentive swellable, sustained-release tablet having a matrix comprised of poly(ethylene oxide) and hydroxypropylmethylcellulose. This dosage form is illustrated in Example 1 and further details may be found in U.S. Patent Application Publication No. 20030104053 to Gusler et al.

In a further embodiment of the present invention, there is provided a dosage form that is formulated to have a large enough size so as to provide for prolonged transit in the upper GI tract. Such tablets would contain at least 800 mg of gabapentin, typically 800-1200 mg. Materials and techniques useful for manufacturing these large-sized dosage forms are described in REMINGTON: THE SCIENCE AND PRACTICE OF PHARMACY, $20^{th}$ edition (Lippincott Williams & Wilkins, 2000) and Ansel et al., PHARMACEUTICAL DOSAGE FORMS AND DRUG DELIVERY SYSTEMS, $6^{th}$ Ed. (Media, Pa.: Williams & Wilkins, 1995). It is preferred that these large size dosage forms are either coated with a membrane or equipped with an osmotic pump system. Suitable membranes include polymer coatings, such as cellulose, cellulose acetate, cellulose acetate butyrate, and ethyl cellulose. Osmotic pumps are described in U.S. Pat. No. 3,845,770 to Theeuwes et al. and U.S. Pat. No. 3,977,404 to Theeuwes.

Numerous materials useful for manufacturing these large-sized dosage forms are described in *Remington: The Science and Practice of Pharmacy*, $20^{th}$ edition (Lippincott Williams & Wilkins, 2000) and Ansel et al., *Pharmaceutical Dosage Forms and Drug Delivery*, $6^{th}$ Ed. (Media, Pa.: Williams & Wilkins, 1995). Along with gabapentin, the core may contain pharmaceutically acceptable additives or excipients to facilitate manufacturing. These include binders (e.g., ethyl cellulose, gelatin, gums, polyethylene glycol, polyvinylpyrrolidone, polyvinylalcohol, starch, sugars, waxes), coloring agents, diluents (e.g., calcium sulfate, cellulose, dicalcium phosphate, kaolin, lactose, mannitol, microcrystalline cellulose, sodium chloride, sorbitol, starch, sucrose), flavoring agents, glidants (e.g., colloidal silicon dioxide, talc), and lubricants (e.g., calcium stearate, glyceryl behenate, hydrogenated vegetable oils, magnesium stearate, polyethylene glycol, sodium stearyl fumarate, stearic acid, stearyl behenate, talc). The core may also contain pharmaceutically acceptable additives or excipients that serve to provide desirable physical characteristics to the dosage form. These include sweeteners, polymers, waxes, and solubility-retarding materials. These dosage forms can be made by techniques that are well established in the art, including wet granulation fluid-bed granulation, dry granulation, direct compression, and so forth.

In another embodiment of the present invention, there is provided a film coated dosage form or a capsule dosage form that allows for the controlled, sustained, and/or extended release of gabapentin in the stomach. In this embodiment, the dosage form may have a drug-containing core surrounded by a controlled release film coating that provides for controlled, sustained, or extended drug release, i.e., continuous diffusion of drug from the core into the upper GI tract.

In certain embodiments, the dosage form may have a drug-containing core surrounded by a swellable coating. See also, US patent application 20030104062, published Jun. 5, 2003 (application Ser. No. 10/213,823) as one potential embodiment of a similar concept.

The controlled release film coating can also be applied by techniques that are well established in the art, for example, by dissolving the material in an appropriate solvent such as acetone or methylene chloride and is then applying the coating to the dosage form core by molding, air spraying, dipping or brushing a solvent-based solution of the material onto the core. Materials suitable for use in controlled release film coatings include by way of illustration, and not limitation, mixtures of waxes such as beeswax and carnuba wax, shellac, and zein, celluloses such as ethyl cellulose, acrylic resins, cellulose acetates including diacetates and triacetates and other cellulose esters, and silicone elastomers. Additional examples are set forth below.

Of particular interest are controlled release film coating materials that can form a semipermeable membrane or coating, which can be porous or non-porous, and which are permeable to external fluid, and substantially impermeable to the unsolubilized drug contained within the core. Typically, external fluids are aqueous fluids or biological fluids in the environment of use, such as the upper GI tract. External fluid passes through the semipermeable membrane into the core, where it solubilizes the drug. The solubilized drug then moves from the core through the membrane into the GI tract.

After application of the controlled release film coating to the core, a drying step is required and then a suitable exit means for the gabapentin must be formed through the semipermeable membrane. Depending on the properties of the gabapentin and other ingredients within the internal compartment and the desired release rate for the dosage form, one or more orifices for gabapentin delivery can be formed through the membrane by mechanical drilling, laser drilling, or the like. The orifice(s) may range in size from a single large orifice containing substantially an entire surface of the dosage form to one or more small orifices selectively located on the surface of the semipermeable membrane. One specific embodiment of a semipermeable membrane-coated core is the elementary osmotic pump. The membrane is provided with one or more delivery orifices, e.g., pierced with a laser to create one or more delivery orifices. Fluid passing through the membrane into the core generates an osmotic pressure that serves to "pump" the solubilized drug through the delivery orifice(s). See, e.g., U.S. Pat. No. 3,845,770 to Theeuwes et al. and U.S. Pat. No. 3,977,404 to Theeuwes.

The materials used in forming the semipermeable membrane can be substantially insoluble in the external fluid or they can erode after a predetermined period of time with erosion taking place at the end of the gabapentin release period. Suitable materials include, by way of illustration and not limitation: acetaldehyde dimethyl acetate and acetaldehyde dimethylcellulose acetate; agar acetate; alkylene oxide and alkyl glycidyl ether copolymers; amylose triacetate; beta glucan acetate and beta glucan triacetate; cellulosic materials, which include cellulose esters (e.g., mono-, di- and tricellulose acetates, cellulose acetate butyl sulfonate, cellulose acetate butyrate, cellulose acetate chloroacetate, cellulose acetate dimethylaminoacetate, cellulose acetate ethyl carbamate, cellulose acetate ethyl carbonate, cellulose acetate ethyl oxalate, cellulose acetate laurate, cellulose acetate methyl carbamate, cellulose acetate methyl sulfonate, cellulose acetate octate, cellulose acetate phthalate, cellulose acetate propionate, cellulose acetate succinate, cellulose acetate p-toluene sulfonate, cellulose acetate valerate, cellulose propionate, cellulose propionate succinate, dimethyl cellulose acetate, mono-, di- and tricellulose acrylates, mono-, di- and tricellulose alkanylates, mono, di and tricellulose aroylates, cellulose triacylates such as cellulose trilaurate, cellulose tripalmitate, cellulose trisuccinate and cellulose trivalerate, and cellulose diacylates such as cellulose dicaprylate, cellulose dioctanoate, cellulose dipalmatate, cellulose dipentanlate and cellulose disuccinate), cellulose ethers (e.g., ethyl cellulose, hydroxyethylcellulose, hydroxypropylcellulose, and methylcellulose), cellulose ester-ether polymers, mono-, di- and tricellulose acrylates, mono-, di- and tricellulose alkenylates; hydroxylated ethylene-vinyl acetate; perm-selective aromatic nitrogen containing polymeric membranes that exhibit water permeability and essentially no solute permeability; polyamides; polyalkylene oxides such as crosslinked and non-crosslinked polyethylene oxide; polyether and polyamide copolymers; polyglycolic acid and polylactic acid and derivatives thereof; polymeric epoxides; poly (methacrylate) copolymer salts such as poly(ammonium methacrylate) copolymer, poly(ammonium methacrylate) copolymer, poly(aminoalkyl methacrylate) copolymer, and (ethyl acrylate)-(methyl methacrylate)-[(trimethylammonium)-ethylmethacrylate] (1:2:0.2) copolymer; cross-linked poly(sodium styrene sulfonate); crosslinked polystyrenes; polyurethanes; polyvinyl alcohol; crosslinked poly(vinylbenzyltrimethyl ammonium chloride); polyvinyl chloride; poly (vinylmethyl ether) copolymers; polyvinylpyrrolidone; propylcarbamate; sulfonated polystyrenes; polyvinylacetate; copolymers of vinyl acetate and vinylpyrrolidone; triacetate of locust gum bean; and so forth; and combinations thereof.

Preferred materials for use in forming the semipermeable membrane include by way of illustration and not limitation, cellulose esters; cellulose ethers; polyvinylpyrrolidone; polyvinyl alcohol; polyalkylene oxides; and combinations thereof.

The semipermeable membrane may also include one or more plasticizers, including: acetylated monoglycerides; dibutyl phthalate, diethyl phthalate, isopropyl phthalate, dimethyl phthalate, and dactyl phthalate; dibutyl sebacate and dimethyl sebacate; esters such as acetyl triethyl citrate, acetyl tributyl citrate, citrate ester, dibutyl sebacate, tetraethyl acetate, triethyl citrate and other citrate esters; fatty acids such as stearic acid; glyceryl behenate; glycols such as 1,2-butylene glycol, 2,3-butylene glycol, diethylene glycol, ethylene glycol, propylene glycol, tetraethylene glycol, triethylene glycol and polyalkylene glycols such as polyethylene glycol; oils such as castor oil and fractionated coconut oil; glycerin; glycerol and glycerol monostearate; triacetin; and so forth; and combinations thereof. Preferred plasticizers include by way of illustration and not limitation, esters and fatty acids.

An example of a core/coating system that can be used with gabapentin to provide for a gastric retentive dosage form is the delayed release tablet described in U.S. Pat. No. 6,350, 471 to Seth, which comprises a drug/excipient core and a coating of a water-insoluble, water-permeable film-forming polymer such as ethyl cellulose, a plasticizer such as stearic acid, and a water-soluble polymer such as polyvinylpyrrolidone or hydroxypropylcellulose.

Another suitable core/coating system has a polyvinyl alcohol coating, which is either a water-soluble polyvinyl alcohol blended with a water insoluble polyvinyl alcohol, or a polyvinyl alcohol that has been crosslinked with a material such as boric acid or sodium borate. Such a coating may also include one or more plasticizers.

Examples 5 to 8 illustrate the formulation of the gastric retentive core/coating dosage forms described above made by wet granulation.

In addition to the active agent and the polymers, the gastric retentive gabapentin dosage forms of the present invention may also include additional excipients, which are known to those of skill in the art to which the invention pertains; such excipients may include, for example, binders, lubricants, diluents, fillers, glidants, and other additives.

Examples of binders that may be used to formulate the dosage forms of the present invention include by way of illustration and not limitation, HPMC, hydroxypropylcellulose ("HPC"), methylcellulose ("MC"), microcrystalline cellulose ("MCC"), ethyl cellulose, polyethylene glycol ("PEG"), polyvinylpyrrolidone ("PVP" also known as povidone), vinylpyrolidone-vinyl acetate copolymer (also known as copovidone), polyvinylalcohol ("PVA"), gelatin, starch, and gums.

Examples of lubricants that may be used to formulate the dosage forms of the present invention include by way of illustration and not limitation, magnesium stearate, calcium stearate, glyceryl behenate, hydrogenated vegetable oils, PED, sodium stearyl fumarate, stearic acid, stearyl behenate, and talc. Examples 1, 2, and 3 describe gastric retentive gabapentin dosage forms formulated using a dry blend process (Examples 1 and 2) or standard granulation (Example 3) with magnesium stearate as a lubricant.

Examples of diluents that may be used to formulate the dosage forms of the present invention include by way of illustration and not limitation, calcium sulfate, cellulose, dicalcium phosphate, kaolin, lactose, mannitol, MCC, sodium chloride, sorbitol, starch, and sucrose.

Fillers may include dicalcium phosphate ("DCP"), MCC, spray-dried lactose, maltose, starch, sugars, sugar alcohols, and waxes; glidants may include colloidal silicon dioxide and talc; and other additives may include coloring agents, flavoring agents, sweeteners, and solubility retarding agents.

For those embodiments of the invention that include further administering additional therapeutic agents simultaneously with gabapentin, these agents can either be administered in the gastric retentive dosage form that includes gabapentin or can be administered in a dosage form that is separate from gabapentin; such dosages can be any suitable formulation as are well known in the art. Where appropriate, the additional therapeutic agent may be contained in a vesicle within the dosage form or as one layer of a bilayer or multilayer dosage form.

For those additional agents where controlled release is desirable, the agent may be incorporated in the gabapentin gastric retentive dosage form or be administered in a separate gastric retentive or other controlled release formulation dosage form. For those additional agents where immediate release is desirable, the agent may be incorporated in a coating around the gabapentin gastric retentive dosage form or in a separate layer of a bilayer tablet, the agent may be simply enclosed in the capsule of the aforementioned gabapentin gastric retentive capsule dosage form, or the agent may be administered in a separate immediate release dosage form.

Typically, dosage forms contain the additional agent (i.e., another analgesic or antineuralgic or anticonvulsant agent) in combination with one or more pharmaceutically acceptable ingredients. The carrier may be in the form of a solid, semi-solid, or liquid diluent, or a capsule. Usually the amount of active agent is about 0.1-95 wt %, more typically about 1-50 wt %. Actual methods of preparing such dosage forms are known, or will be apparent, to those skilled in this art (see, e.g., REMINGTON: THE SCIENCE AND PRACTICE OF PHARMACY, $20^{th}$ addition (Lippincott Williams & Wilkins, 2000)). The dosage form to be administered will, in any event, contain a quantity of the additional therapeutic agents in an amount effective to alleviate the symptoms of the subject being treated.

In the preparation of pharmaceutical formulations containing the additional therapeutic agent in the form of dosage units for oral administration the agent may be mixed with solid, powdered ingredients, such as lactose, microcrystalline cellulose, maltodextrin, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate, and polyethylene glycol waxes. The mixture is then processed into granules or pressed into tablets such as chewable and oral disintegrating tablets.

Soft gelatin capsules may be prepared by mixing the active agent and vegetable oil, fat, or other suitable vehicle. Hard gelatin capsules may contain granules of the active agent, alone or in combination with solid powdered ingredients such as lactose, saccharose, sorbitol, mannitol, potato starch, cornstarch, amylopectin, cellulose derivatives, or gelatin.

Liquid preparations for oral administration may be prepared in the form of syrups or suspensions, e.g. solutions or suspensions containing about 0.2-20 wt % of the active agent and the remainder consisting of sugar or sugar alcohols and a mixture of ethanol, water, glycerol, propylene glycol, and PEG. The liquid preparations may contain coloring agents, flavoring agents, sweeteners such as saccharin, and carboxymethyl cellulose or other thickening agents. Liquid preparations for oral administration may also be prepared in the form of a dry powder to be reconstituted with a suitable solvent prior to use.

When the method of the invention includes administering another agent, such as secondary analgesics, anticonvulsant agent, antidepressants, or opioids, the additional agent may be obtained from a commercial source in a variety of dosage forms (e.g., tablets, capsules, oral suspensions, and syrups). The additional agent may be administered as a separate dosage form or the gastric retentive gabapentin dosage form of the present invention may be designed to include the additional agent. Additional analgesic agents may be selected from among the many available NSAIDs on the market. Examples of suitable commercially available anti-convulsants include TEGRETOL® (carbamazepine; Novartis, Summit, N.J.), DILANTIN® (Pfizer Inc., New York, N.Y.), and LAMICTAL® (lamotrigine (GlaxoSmithKline, Philadelphia, Pa.). Suitable antidepressants include the tricyclic antidepressants LIMBITROL® (amitriptyline; Hoffmann-LaRoche, Nutley, N.J.), TOFRANIL® (imipramine; Tyco Healthcare, Mansfiled, Mass.), ANAFRANL™ (clomipramine; Tyco Healthcare, Mansfield, Mass.), and NOR-PRAMIN® (desipramine; Sanofi-Aventis, Bridgewater, N.J.). Examples of suitable commercially available opioids include PERCOCET® (oxycodone; Dupont Merck Pharmaceuticals, Wilmington, Del.), ULTRACET® (tramadol; Johnson & Johnson, New Brunswick, N.J.), and CLONOPIN™ (clonazepam; Hoffmann-LaRoche, Nutley, N.J.).

Utility

As previously discussed, the gastric retentive dosage forms of the present invention reduce the side effects that have been reported with conventional immediate release gabapentin dosage forms. The dosage forms of the present invention are comprised of a therapeutically effective amount of gabapentin, pregabalin, another GABA analog, or a pharmaceutically acceptable salt thereof, to a patient in need of such treatment in a gastric retentive dosage form that is administered to the patient in a once-daily or twice-daily dosing regimen. Examples of conditions that may benefit from the gastric retentive dosage forms of the present invention include all conditions that are treatable with immediate release gabapentin, such as for example, seizures, PHN, neuropathic pain, restless legs syndrome, essential tremor, bipolar disorder, migraine headaches, and the symptoms associated with hormonal imbalances and chemotherapy. Within the context of hormonal imbalances, the gastric retentive dosage forms may be used to reduce or eliminate the severity of menopausal hot flashes and within the context of chemotherapy, the gastric retentive dosage forms may be used to reduce or eliminate the severity of chemotherapy-related nausea and hot flashes.

All patent applications, patents, publications, and other published documents mentioned or referred to in this specification are incorporated herein by reference in their entireties, to the same extent as if each individual patent application, patent, publication, and other published document was specifically and individually indicated to be incorporated by reference.

The general methods of the invention are best understood with reference to the following examples which are intended to enable those skilled in the art to more clearly understand and to practice the present invention. The following examples are not intended, nor are they to be construed, as limiting the scope of the invention, but are merely intended to be illustrative and representative of the invention.

EXPERIMENTAL

The practice of the present invention will use, unless otherwise indicated, conventional techniques of pharmaceutical formulation, medicinal chemistry and the like, which are within the skill of the art. Such techniques are explained fully in the literature. Preparation of various types of pharmaceutical formulations are described, for example, in REMINGTON: THE SCIENCE AND PRACTICE OF PHARMACY, 20$^{th}$ addition (Lippincott Williams & Wilkins, 2000) and Ansel et al., PHARMACEUTICAL DOSAGE FORMS AND DRUG DELIVERY SYSTEMS, 6$^{th}$ Ed. (Media, Pa.: Williams & Wilkins, 1995).

In all human clinical trials described in the examples, all investigators involved in the studies conducted the clinical trials in accordance with the International Conference on Harmonization Harmonized Tripartite Guideline for Good Clinical Practice, the Guidelines of the Declaration of Helsinki, Finland, 1964 and its subsequent amendments up through at least 1996 (Tokyo, Japan, 1975; Venice, Italy, 1983; Hong Kong, 1989; Republic of South Africa, 1996; and Scotland 2000), and either United States IND regulations (21. C.F.R. §§50, 54 and 56) and all other national, state and local laws if conducted within the United States or applicable national, sate, and local laws of the pertinent regulatory authorities if conducted outside the United States. All patients provided written Informed Consent before any study-related procedures were undertaken.

Gabapentin was obtained from a variety of sources, including Plantex U.S.A. (Englewood Cliffs, N.J.). METHOCEL® brand hydroxypropyl methylcellulose (also known as hypromellose), and SENTRY® POLYOX® brand polyethylene oxide were obtained from Dow Chemical (Midland, Mich.). METHOCEL® E5, premium is a USP type 2910 hydroxypropyl methylcellulose with number average molecular weight of on the order of 6000-8000 and a viscosity of 5 cps as a 2% aqueous solution at 20° C. METHOCEL® K4M and METHOCEL® K15M are USP type 2208 hydroxypropyl methylcellulose with viscosities of 4000 cps and 15,000 cps, respectively, as a 2% aqueous solution at 20° C., and number average molecular weights on the order of 80,000 and 100,000, respectively. SENTRY® POLYOX® WSR 301, NF FP, SENTRY® POLYOX® WSR Coagulant, NF FP and SENTRY® POLYOX® WSR 303, NF FP have viscosity-average molecular weights of approximately 4,000,000, 5,000,000 and 7,000,000, respectively. AVICEL PH-101, NF is microcrystalline cellulose supplied by FMC Corporation (Philadelphia, Pa.). Magnesium stearate, NF was supplied by Spectrum Quality Products (New Brunswick, N.J.) or an alternative supplier.

Example 1

Gastric retentive gabapentin tablets were manufactured using a dry blend process, and hand made on a Carver Auto C Press (Fred Carver, Inc., Indiana). The dry blend process consisted of blending all of the ingredients in a plastic bag, and compressing into a 1000 mg tablet (600 mg gabapentin dose) using a 0.7086"×0.3937" Mod Oval die (Natoli Engineering, St. Charles, Mo.). The parameters for the operation of the Carver Auto C Press were as follows: 4000 lbs force, 0-second dwell time (the setting on the Carver Press), and 100% pump speed. The formulation for the tablets is set froth in Table 1:

TABLE 1

| SAMPLE NO. | FORMULATION COMPOSITION (wt %) | | | |
|---|---|---|---|---|
| | GABAPENTIN | PEO COAGULANT | METHOCEL® K100M | MAGNESIUM STEARATE |
| 1 | 60.0 | 39.0 | 0.0 | 1 |
| 2 | 60.0 | 24.3 | 14.7 | 1 |
| 3 | 60.0 | 0.0 | 39.0 | 1 |

The dissolution was determined in USP apparatus 1 (40 mesh baskets), 100 rpm, in deionized water. Samples, 5 ml at each time-point, were taken without media replacement at 1, 4, and 8 hours. The resulting cumulative dissolution profile, based upon a theoretical percent active added to the formulations, is set forth in Table 2:

TABLE 2

| TIME (HOURS) | THEORETICAL wt % OF ACTIVE RELEASED | | |
|---|---|---|---|
| | SAMPLE 1 | SAMPLE 2 | SAMPLE 3 |
| 1 | 15.4 | 14.8 | 18.6 |
| 4 | 39.4 | 37.4 | 43.3 |
| 8 | 61.7 | 57.8 | 64.7 |

Example 2

Gastric retentive gabapentin tablets were manufactured using a dry blend process, and hand made on a Carver Auto C Press (Fred Carver, Inc., Indiana). The dry blend process consisted of blending all of the ingredients in a plastic bag, and compressing into a 600 mg tablet (300 mg gabapentin) using a 0.6299"×0.3937" Mod Oval die (Natoli Engineering, St. Charles, Mo.). The parameters for the operation of the Carver 'Auto C' Press were as follows: ~2000-2500 lbs. force, 0-second dwell time (the setting on the Carver Press), and 100% pump speed. The formulation for the tablets is set forth in Table 3:

TABLE 3

| SAMPLE NO. | FORMULATION COMPOSITION (wt %) | | | |
|---|---|---|---|---|
| | ACTIVE | PEO COAGULANT | METHOCEL® K15M | MAGNESIUM STEARATE |
| 4 | 50.0 | 24.5 | 24.50 | 1 |

The dissolution was determined in USP apparatus 1 (40 mesh baskets), 100 rpm, in deionized water. Samples, 5 ml at each time-point, were taken without media replacement at 1, 2, 4, 6, 8 and 10 hours. The resulting cumulative dissolution profile, based upon a theoretical percent active added to the formulation is set forth in Table 4:

TABLE 4

| TIME (HOURS) | THEORETICAL wt % OF ACTIVE RELEASED SAMPLE 4 |
|---|---|
| 1 | 20.6 |
| 2 | 32.4 |
| 4 | 49.7 |
| 6 | 63.1 |
| 8 | 74.0 |
| 10 | 82.6 |

Example 3

Three gastric retentive gabapentin formulations were manufactured utilizing a standard granulation technique. The formulations manufactured are shown Table 5.

TABLE 5

GR GABAPENTIN FORMULATIONS

| GABAPENTIN GR6, 300-MG (GR6. 300-MG) | GABAPENTIN GR8, 300-MG (GR8, 300-MG) | GABAPENTIN GR8, 600-MG (GR8, 600-MG) |
|---|---|---|
| 44.76% Gabapentin | 44.76% Gabapentin | 61.11% Gabapentin |
| 16.46% METHOCEL ® K4M. premium | 21.99% METHOCEL ® K15M, premium | 7.59% METHOCEL ® K15M, premium |
| 21.99% SENTRY ® POLYOX ® WSR 303, NF FP | 21.99% SENTRY ® POLYOX ® WSR Coagulant, NF FP | 27.09% SENTRY ® POLYOX ® WSR 303, NF FP |
| 12.98% AVICEL ® PH-101, NF | 7.49% AVICEL ® PH-101, NF | 0.00% AVICEL ® PH-101, NF |
| 2.75% METHOCEL ® E5, premium | 2.75% METHOCEL ® E5, premium | 3.22% METHOCEL ® E5, premium |
| 1.00% Magnesium Stearate, NF | 1.00% Magnesium Stearate, NF | 1.00% Magnesium Stearate, NF |
| 670-mg | 670-mg | 982-mg |
| 0.3937" x 0.6299" Mod Oval | 0.3937" x 0.6299" Mod Oval | 0.4062" x 0.75" Mod Cap |

The dissolution profiles, as determined by USP Apparatus 1 (100 rpm) in modified simulated gastric fluid, for three prototypes formulations are shown in FIG. 1.

Example 4

The pharmacokinetic profiles of the three gastric retentive ("GR") formulations described in Example 3, administered as a 600-mg dose, were compared to NEURONTIN® immediate release 300-mg capsule in a randomized four-way cross-over experiment involving 15 healthy volunteers. Each subject was administered treatment of 600-mg gabapentin as one of the three formulations (1×600-mg tablet or 2×300-mg tablet) or NEURONTIN® capsules (2×300-mg) within 5 minutes of completing a high fat breakfast (FDA breakfast). Plasma samples were taken up to 48 hours post-dose. FIG. 2 illustrates the average plasma profile for the four treatments administered, and the pharmacokinetic data are shown in Table 6.

TABLE 6

GABAPENTIN PLASMA DATA - AVERAGE FOR 15 SUBJECTS

| DOSING | | #$AUC_{inf}$ (µg/ml)*hr) | *$C_{max}$ (µg/ml) | *$T_{max}$ (hours) |
|---|---|---|---|---|
| NEURONTIN ®, 300-mg 2 x capsules | Mean % CV | 46.65 19.0 | 4.72 20.2 | 3.93 15.1 |
| GR6, 300-mg 2 x tablets | Mean % CV | 44.43 34.9 | 2.97 29.7 | 6.63 45.1 |
| GR8, 300-mg 2 x tablets | Mean % CV | 41.84 34.4 | 3.10 26.2 | 5.63 34.9 |
| GR8, 600-mg 1 x tablet | Mean % CV | 48.01 26.8 | 3.13 18.7 | 7.13 42.2 |

Geometric Mean and Geometric % CV (coefficient of variation) are reported here
*Arithmetic mean
$AUC_{inf}$ = area under the concentration-time curve from time zero to infinity.

As demonstrated in Table 6 and FIG. 2, the gastric retentive (GR) formulations of the present invention demonstrated sustained release with a lower maximum plasma concentration ($C_{max}$) and a larger value for the time of the maximum concentration ($T_{max}$) compared to the immediate release (IR) capsules without any significant loss in the bioavailability of the gabapentin as measured by the plasma $AUC_{inf}$. The $C_{max}$ for the GR dosage forms were approximately 30% to approximately 40% lower (rounded to the nearest 5%) than the $C_{max}$ for the IR dosage form. The $T_{max}$ for each of the three GR dosage ranged from 1.5 to 3.5 hours longer than the $T_{max}$ for the IR dosage form, which indicates that $T_{max}$ for the gastric retentive dosage form of the present invention is approximately 40% to approximately 80% slower (rounded to the nearest 5%) than $T_{max}$ for immediate release dosages forms.

Example 5

A gastric retentive tablet containing 900 mg of gabapentin is prepared by granulation with 90 mg of PVP and 10 mg of magnesium stearate and then tableted as a 1000 mg tablet on a Carver press with 4000 lbs force, 0-second dwell time. These tablet cores are then coated from an alcohol-water solution that dries with approximately 2% dry coat weight of 10 mg ethyl cellulose, 7 mg PVP, and 3 mg stearic acid.

Example 6

A gastric retentive tablet containing 1200 mg of gabapentin is prepared by granulation with 120 mg of PVP and 10 mg of magnesium stearate and then tableted as a 1330 mg tablet on a Carver press with 4000 lbs force, 0-second dwell time. These tablet cores are then coated from an alcohol-water solution that dries with approximately 25 mg dry coat weight of 10 mg ethyl cellulose, 10 mg HPC, and 5 mg glyceryl behenate.

Example 7

A gastric retentive tablet containing 900 mg of gabapentin is prepared by granulation with 90 mg of PVP and 10 mg of magnesium stearate and then tableted as a 1000 mg tablet on a Carver press with 4000 lbs force, 0-second dwell time. These tablet cores are then coated from an aqueous solution that dries with approximately 2% dry coat weight of 15 mg PVA, 5 mg PVP, and 3 mg stearic acid. The coated tablets are then sprayed with an aqueous solution of 1% sodium borate to crosslink the PVA and dried.

Example 8

A gastric retentive tablet containing 900 mg of gabapentin is prepared by granulation with 90 mg of PVP, 250 mg MCC, and 10 mg of magnesium stearate and then tableted as a 1250 mg tablet on a Carver press with 4000 lbs force, 0-second dwell time. These tablet cores are then coated from an alcohol-water solution that dries with approximately 2% dry coat weight of 10 mg ethyl cellulose, 7 mg PVP, and 3 mg stearic acid.

Example 9

To study the rate and extent of absorption of the gastric retentive gabapentin dosage forms of the present invention, a four-arm, non-randomized, open-label, single dose, fed designed study was conducted on 24 healthy non-smoking males.

The objective of the study was to compare the rate and extent of absorption of gabapentin following administration of four escalating doses of a test formulation of 600 mg tablets of gastric retentive gabapentin (Depomed Inc., Menlo Park, Calif.) administered once daily under fed condition.

The subjects of the study were 24 nonsmoking males in the age range of 18-65 years old. The 24 subjects were separated into four treatment groups of six subjects per group. The drug administration protocol was as follows:

TREATMENT GROUP A—following an overnight fast of at least 10 hours, one 600 mg gastric retentive gabapentin tablet with 240 mL of ambient temperature water was administered 20 minutes after the start of a standardized moderate fat content meal. Treatment dose was 600 mg.

TREATMENT GROUP B—following an overnight fast of at least 10 hours, two 600 mg gastric retentive gabapentin tablets with 240 mL of ambient temperature water were administered 20 minutes after the start of a standardized moderate fat content meal. Treatment dose was 1200 mg.

TREATMENT GROUP C—following an overnight fast of at least 10 hours, three 600 mg gastric retentive gabapentin tablets with 240 mL of ambient temperature water were administered 20 minutes after the start of a standardized moderate fat content meal. Treatment dose was 1800 mg.

TREATMENT GROUP D—following an overnight fast of at least 10 hours, four 600 mg gastric retentive gabapentin tablets with 240 mL of ambient temperature water were administered 20 minutes after the start of a standardized moderate fat content meal. Treatment dose was 2400 mg.

The meals for all the treatment groups were a 500-600 calorie meal with moderate fat (about 40% fat), with approximately 80 calories from protein, 252 calories from carbohydrates, and about 207 calories from fats. As noted above, the meals were provided after an overnight fast of at least 10 hours. Additional moderate fat meals with beverages were provided for the subjects at 4.5 and 9.5 hours post-dose and a standardized snack was provided 13.5 hours post-dose. All meals and beverages were free of alcohol, grapefruit products, xanthine, and caffeine and were identical during the study periods.

The length of the study was four three-day periods separated by at least one-week washout period between treatments. Eighteen blood samples of 4 mL each were drawn in each three-day-period according to the following schedule (in hours): 0.0 (pre-dose), 0.5, 1.0, 2.0, 3.0, 4.0, 5.0, 6.0, 7.0, 8.0, 10.0, 12.0, 14.0, 16.0, 24.0, 35.0, and 36.0 hours post-dose. The total blood volume was 315 mL. Vital signs (blood pressure, temperature, respiration rate, and heart rate) were measured at the following time periods: 0.0 (predose), 2.0, 4.0, 8.0, 12.0, and 24.0 hours post dose. Data obtained from the study is shown in Tables 7 and 8 and in FIG. 4. Data reported in table 7 represents the arithmetic mean.

TABLE 7

| DOSE (mg) | $C_{max}$ FOR GR GABAPENTIN (µg/mL) |
|---|---|
| 600 | 2.96 |
| 1200 | 4.93 |
| 1800 | 6.68 |
| 2400 | 7.85 |

TABLE 8

| DOSE (mg) | AUC FOR GR GABAPENTIN (ng-h/mL)[1,2] |
|---|---|
| 400 | 25000 |
| 600 | 36247 |
| 800 | 42000 |
| 1200 | 63765 |
| 1500 | 79000 |
| 1600 | 80000 |
| 1800 | 91147 |
| 2000 | 99000 |
| 2400 | 108677 |
| 2500 | 110000 |
| 3000 | 120000 |

[1] Some data is extrapolated or interpolated - 600 mg, 1200 mg, 1800 mg, and 2400 mg are actual data
[2] AUC values reported here are the arithmetic mean $AUC_{0-t}$ where t is 36 hours for 19 subjects To determine the rate and extent of absorption of the gastric retentive gabapentin dosage forms, the pharmacokinetic measurements obtained for the AUC (in ng-h/mL) for each treatment group at 24 hours (Table 8) was plotted against the amount of drug administered to each group. A comparison of the data for the GR and IR gabapentin in FIGS. 3 and 4 demonstrate the enhanced bioavailability of the gastric retentive gabapentin at high doses of the present invention. As shown in FIG. 4, patients were administered 600 mg, 1200 mg, 1800 mg, and 2400 mg of gastric retentive gabapentin in once-daily dosings (AUC values for the additional dosages of the GR gabapentin in Table 8 and FIG. 4 were extrapolated based upon the curve of FIG. 4). FIG. 3 shows the same experiment conducted with 400 mg, 800 mg, 1200 mg, and 1600 mg of immediate release gabapentin. The nearly linear curve of FIG. 4 of AUC up to 24 hours demonstrates, the gastric retentive gabapentin dosage forms of the present invention demonstrated continued bioavailability at doses as high as 2400 mg. By contrast, the plateau seen in FIG. 3 after 1200 mg of IR gabapentin indicates that the body is incapable of effectively absorbing more drug as the dose increases above 1200 mg of IR gabapentin.

The difference in bioavailability of gastric retentive and immediate release gabapentin depicted in FIGS. 4 and 3 is shown more dramatically in FIGS. 6, and 5, respectively, where the log(AUC) is plotted against the dosage. The log graphs show the sharp decline in bioavailability of immediate release gabapentin with the 1200 mg dosing. By contrast, even at a dosing of 1800 mg, the gastric retentive gabapentin of the present invention demonstrates continued bioavailability of the drug (FIG. 6).

Further evidence of enhanced bioavailability of at least one embodiment of the present invention, as shown in FIGS. 4 and 6 is obtained by comparing the data on a dose-normalized basis. According to the Summary Basis of Approval for NEUROTNIN® (New Drug Application ("NDA") 20-235), the normalized $AUC_{(600-mg)}$ of 600-mg, 800-mg, 1200 mg and 1600-mg in four subjects were 53%, 37%, 38% and 29%, respectively where the AUC was obtained at steady-state. For one embodiment of the present invention, the geometric mean (19 subjects) values of $AUC_{0-x}$ (ng*hr/ml) values for escalating doses of 600-mg, 1200-mg, 1800-mg and 2400-mg administered as single-doses immediately after a meal to healthy volunteers were 35698, 63209, 90894, and 108572, respectively (rounded to the nearest whole number). Because the $AUC_{0-x}$ for a single dose is equivalent to the steady-state AUC as measured between dosing intervals, the AUC values in both cases represent the $AUC_{0-x}$, and comparisons can be made. Therefore, if a ratio of the AUC to that obtained at 600-mg dose, and normalized for the dose administered is made, the ratios for the NEUROTNIN® capsules are 1.0, 0.698, 0.717 and 0.547 for the 600-mg, 800-mg, 1200 mg and 1600-mg respectively compared to ratios for one embodiment of the present invention of 1.0, 0.882, 0.843 and 0.753 for the 600-mg, 1200-mg, 1800-mg and 2400-mg doses, respectively. Thus, the fraction of the dose that is absorbed decreases by about 50% when the dose is increased from 600-mg to 1600 mg for NEUROTNIN® capsules. In contrast, for one embodiment of the present invention, the fraction of the dose that is absorbed decreases by about 25% when the dose is increased from 600 mg to 2400 mg, and only 15% at 1800 mg, which is still above the 1600 mg dose of immediate release NEURONTIN® which demonstrated a loss of almost 50% compared to the 600-mg dose of immediate release NEURONTIN®.

Example 10

To study the efficacy of once-daily versus twice-daily administration of gastric retentive gabapentin, a randomized, double-blind multi-center trial was conducted on 158 patients (consisting of both males and females older than 18 years of age) with PHN. The aim of the study was to determine if the gastric retentive gabapentin dosage forms was successful in reducing the patients' mean daily pain scores from the baseline week to end of the efficacy treatment period (Treatment Week 4). Secondary efficacy measures included changes from baseline in mean weekly sleep interference scores, Short-Form McGill Pain Questionnaire (SF-MPQ), the Neuropathic Pain Scale (NPS), Patient Global Impression of Change (PGIC), and Investigator-rated Clinical Global Impression of Change (CGIC).

Patients suffering from PHN were eligible for the study if they had experienced pain for at least three months after the healing of an acute herpes zoster skin rash with a pain intensity of at least 4 on the 11-point Lickert scale (i.e., 0-10) at screening. Baseline pain values for all eligible patients were determined during a one-week pretreatment period where the patients were to base their pain during this week on the 11-point Lickert scale; patients who recorded at least a 4 on the 11-point scale together with the completion of at least 4 days of diary entries were deemed eligible to participate in the study. All patients were required to undergo 7-day washout for medications prescribed for PHN and a 14-day washout (tapered appropriately) for strong opiates (i.e., morphine or fentanyl). Patients were permitted to take acetaminophen or acetaminophen with hydrocodone (if required for treatment of pain during the study).

The 158 patients selected for the study were randomly assigned to treatment with 1800 mg of gastric retentive gabapentin dosed once daily following the evening meal (55 patients), or dosed twice daily with 600 mg in the morning and 1200 mg in the evening (52 patients) against a placebo (51 patients). The course of the study was five weeks. Patients randomized to active treatment were gradually titrated over a two-week period to a total daily dose of 1500 mg, followed by an additional two-week period at the 1800 mg/day maintenance dose. All patients, regardless of treatment, took the same number of tablets of identical appearance each day to maintain the study blind; accordingly, patients assigned to placebo received no drug, but took the same number of tablets each day as those patients assigned to active treatments. A one week blinded tapering period followed the four-week efficacy treatment period. End of study safety assessments were completed at the Week 5 visit.

The gastric retentive gabapentin dosage units prepared for administration to the patients were 300 mg and 600 mg white film coated, modified oval-shaped tablets with a total mass of 714 mg and 1020 mg, respectively. In addition to gabapentin, the tablets included the following inactive ingredients: polyethylene oxide, hypromellose, magnesium stearate, and coating, and the 300 mg dose also included MCC. The placebo tablets were coated to match the appearance of the active tablets.

Patients assigned to placebo randomly took the required number of placebo tablets each morning and evening to match the dosing of patients assigned to the two active treatment groups.

The results of the study are shown in Tables 9-13. In all tables, patients who had both baseline and endpoint values were included in the data analysis. In accordance with standard statistical analyses, a lower p-value represents stronger evidence against the null hypothesis of no effect in the population being tested (p=1.00).

In Tables 9, 10, and 12 the "p-values" (both overall and vs. placebo) are based on a Type III sum of squares statistical analysis; the LS mean and SEM values for the Baseline are estimated from the ANOVA (ANalysis Of VAriance between groups) model that includes treatment, center, and treatment by center interaction factor; and the LS mean and SEM values for the Endpoint and Change from Baseline to Endpoint are estimated from the ANCOVA (ANalysis of COVAriance) model that includes treatment, center, treatment by center interaction factor, and baseline value as a covariate.

In Table 10, the "responders" are defined as patients with at least 50% reduction in LOCF average daily pain score from baseline; the "overall p-value" is based on a Cochran-Mantel-Haenszel test for the general association stratified by the baseline pain score category (less than 8 vs. at least 8); and the "p-value vs. placebo" is based on the Z test for the difference in proportions between the two groups (i.e., the treatment groups and the placebo group).

TABLE 9

ANALYSIS OF LOCF AVERAGE DAILY PAIN SCORE

| AVERAGE DAILY PAIN SCORE | TREATMENT GROUP | | | |
|---|---|---|---|---|
| | GR GABAPENTIN (1800 mg PM) n = 55 | GR GABAPENTIN (1800 mg AM/PM) n = 52 | PLACEBO n = 51 | OVERALL TREATMENT p-value |
| Baseline | | | | |
| Mean (SD) | 6.56 (1.43) | 6.32 (1.27) | 6.59 (1.58) | 0.528 |
| LS Mean (SEM) | 6.54 (0.20) | 6.28 (0.21) | 6.56 (0.21) | |

TABLE 9-continued

ANALYSIS OF LOCF AVERAGE DAILY PAIN SCORE

| AVERAGE DAILY PAIN SCORE | GR GABAPENTIN (1800 mg PM) n = 55 | GR GABAPENTIN (1800 mg AM/PM) n = 52 | PLACEBO n = 51 | OVERALL TREATMENT p-value |
|---|---|---|---|---|
| 95% CI | (6.13, 6.94) | (5.87, 6.69) | (6.14, 6.97) | |
| p-value (vs. placebo) | 0.943 | 0.315 | | |
| *LOCF Endpoint* | | | | |
| Mean (SD) | 4.69 (2.20) | 4.21 (2.27) | 5.32 (2.09) | 0.042 |
| LS Mean (SEM) | 4.56 (0.28) | 4.25 (0.29) | 5.20 (0.29) | |
| 95% CI | (4.00, 5.12) | (3.68, 4.82) | (4.62, 5.78) | |
| *Change from Baseline to LOCF Endpoint* | | | | |
| Mean (SD) | −1.87 (1.78) | −2.11 (2.12) | −1.27 (1.93) | 0.042 |
| LS Mean (SEM) | −1.93 (0.28) | −2.24 (0.29) | −1.29 (0.29) | |
| 95% CI | (−2.49, −1.37) | (−2.81, −1.67) | (−1.86, −0.71) | |
| *GR Gabapentin minus Placebo* | | | | |
| LS Mean Δ (SEM) | −0.64, (0.37) | −0.95 (0.38) | N/A | |
| 95% CI for Δ | (−1.38, 0.10) | (−1.71, −0.20) | | |
| p-value (vs. placebo) | 0.089 | 0.014 | | | n = sample size;
GR = gastric retentive;
LOCF = last observation carried forward;
LS = least squares;
SEM = standard error of LS mean;
CI = confidence interval;
Δ = Difference;
N/A = not applicable The Overall Treatment p-values in Table 9 show that the group as a whole experienced a statistically significant decrease in pain from Baseline to LOCF. While Table 9 shows a relatively large placebo effect, most likely due to self administration of acetaminophen (with or without hydrocodone) during the course of the study, the p-values (vs. placebo) for the two gabapentin treatment groups indicate a statistically significant decrease in the pain experienced by the patients from Baseline to LOCF (see, p-values (vs. placebo) at Baseline and for GR Gabapentin minus Placebo). Between the two treatment groups, patients administered the twice-daily gastric retentive gabapentin showed more pain reduction than did the patients on the once-daily dosing regimen; however, the difference was not great (see, values for LOCF Endpoint and Changes from Baseline to LOCF Endpoint).

Table 10 shows that 25.5% of the patients following the once-daily dosing regimen and 28.8% of the patients following the twice-daily dosing regimen experienced a 50% reduction in pain from Baseline to LOCF and Table 11 outlines the pain reduction from 0% Decrease to 100% Decrease for each of the patients in each of the Treatment Groups. Within the once-daily Treatment Group, two patients reported a 90% decrease in pain and within the twice-daily Treatment Group, three patients reported a 100% decrease.

TABLE 10

PROPORTION OF RESPONDERS AT ENDPOINT

| AVERAGE DAILY PAIN SCORE | GR GABAPENTIN (1800 mg PM) n = 55 | GR GABAPENTIN (1800 mg AM/PM) n = 52 | PLACEBO n = 51 | OVERALL TREATMENT p-value |
|---|---|---|---|---|
| *Responders at Endpoint* | | | | |
| Yes | 14 (25.5%) | 15 (28.8%) | 6 (11.8%) | 0.094 |
| No | 41 (74.5%) | 37 (71.2%) | 41 (88.2%) | |
| *GR Gabapentin minus Placebo* | | | | |
| Δ in Yes Responders | 13.70% | 17.00% | N/A | |
| 95% CI of ΔP | (−0.83%, 28.23%) | (1.84%, 32.16%) | | |
| p-value (vs. placebo) | 0.072 | 0.032 | | | n = sample size;
GR = Gastric Retentive;
Δ = Difference;
ΔP = Difference in proportions;
N/A = not applicable

TABLE 11

PERCENT CHANGE FROM BASELINE TO ENDPOINT IN LOCF AVERAGE DAILY PAIN SCORE

| AVERAGE DAILY PAIN SCORE | TREATMENT GROUP | | |
|---|---|---|---|
| | GR GABA-PENTIN (1800 mg PM) n = 55 | GR GABA-PENTIN (1800 mg AM/PM) n = 52 | PLACEBO n = 51 |
| Percent Change from Baseline to LOCF Endpoint: n(%) | | | |
| Any Increase | 6 (10.91%) | 5 (9.72%) | 12 (23.53%) |
| No Change | 2 (3.64%) | 3 (5.77%) | 5 (8.80%) |
| >0% Decrease | 47 (85.45%) | 44 (84.62%) | 34 (66.67%) |
| ≥10% Decrease | 40 (72.73%) | 39 (75.00%) | 33 (64.71%) |
| ≥20% Decrease | 31 (56.36%) | 31 (59.62%) | 23 (45.10%) |
| ≥30% Decrease | 24 (43.64%) | 25 (48.08%) | 16 (31.37%) |
| ≥40% Decrease | 18 (32.73%) | 19 (36.54%) | 11 (21.57%) |
| ≥50% Decrease | 14 (25.45%) | 15 (28.85%) | 6 (11.76%) |
| ≥60% Decrease | 9 (16.36%) | 11 (21.15%) | 5 (9.80%) |
| ≥70% Decrease | 3 (5.45%) | 10 (19.23%) | 3 (5.88%) |
| ≥80% Decrease | 3 (5.45%) | 7 (13.46%) | 0 (0.00%) |
| ≥90% Decrease | 2 (3.64%) | 4 (7.69%) | 0 (0.00%) |
| =100% Decrease | 0 (0.00%) | 3 (5.77%) | 0 (0.00%) | n = sample size;
LOCF = last observation carried forward

Table 12 sets forth the LOCF Average Daily Pain Score from Table 9 for those patients at least 65 years of age, The data from Table 12 shows statistical differences from placebo in pain management between the patients on the once-daily dosing regimen and the twice-daily dosing regimen (see, p-value (vs. placebo) for GR Gabapentin minus Placebo) and is more consistent than for the complete age group (Table 9).

TABLE 12

ANALYSIS OF LOCF AVERAGE DAILY PAIN SCORE FOR PATIENTS OF AT LEAST 65 YEARS OF AGE

| AVERAGE DAILY PAIN SCORE | TREATMENT GROUP | | | OVERALL TREATMENT p-value |
|---|---|---|---|---|
| | GR GABAPENTIN (1800 mg PM) n = 41 | GR GABAPENTIN (1800 mg AM/PM) n = 38 | PLACEBO n = 33 | |
| Baseline | | | | |
| Mean (SD) | 6.46 (1.57) | 6.18 (1.58) | 6.68 (1.58) | 0.362 |
| LS Mean (SEM) | 6.46 (0.23) | 6.18 (0.24) | 6.68 (0.26) | |
| 95% CI | (6.01, 6.92) | (5.71, 6.65) | (6.17, 7.18) | |
| p-value (vs. placebo) | 0.532 | 0.158 | | |
| LOCF Endpoint | | | | |
| Mean (SD) | 5.81 (2.21) | 4.37 (2.26) | 5.89 (2.17) | 0.033 |
| LS Mean (SEM) | 4.79 (0.28) | 4.60 (0.29) | 5.67 (0.31) | |
| 95% CI | (4.23, 5.34) | (4.02, 5.18) | (5.05, 629) | |
| Change from Baseline to LOCF Endpoint | | | | |
| Mean (SD) | −1.65 (1.71) | −1.80 (2.12) | −0.79 (1.42) | 0.033 |
| LS Mean (SEM) | −1.64 (0.28) | −1.83 (0.29) | −0.76 (0.31) | |
| 95% CI | (−2.20, −1.09) | (−2.41, −1.25) | (−1.38, −0.14) | |
| GR Gabapentin minus Placebo | | | | |
| LS Mean Δ (SEM) | −0.88 (0.42) | −1.07 (0.43) | N/A | |
| 95% CI for Δ | (−1.71, −0.05) | (−1.92, −0.22) | | |
| p-value (vs. placebo) | 0.037 | 0.014 | | | n = sample size;
GR = gastric retentive;
LOCF = last observation carried forward;
LS = least squares;
SEM = standard error of LS mean;
CI = confidence interval;
Δ = Difference;
N/A = not applicable

Example 11

To study the efficacy of once-daily and twice-daily administration of gastric retentive gabapentin (gabapentin GR) versus placebo, a randomized, double-blind multi-center placebo controlled trial was conducted on 147 patients (consisting of both males and females not less than 18 years of age) with painful diabetic peripheral neuropathy (DPN). The aim of the study was to determine if the gastric retentive gabapentin GR dosage forms were successful in reducing the patients' mean daily pain scores from the Baseline week to end of the efficacy treatment period (Treatment Week 4). Secondary efficacy measures included changes from Baseline in mean weekly sleep interference scores, Short-Form McGill Pain Questionnaire (SF-MPQ), the Neuropathic Pain Scale (NPS), Patient Global Impression of Change (PGIC), and Investigator-rated Clinical Global Impression of Change (CGIC).

Patients with a diagnosis of type 1 or type 2 diabetes were eligible for the study if they had experienced symmetrical painful symptoms in distal extremities for 1-5 years and the symptoms were attributable to sensorimotor diabetic peripheral neuropathy (DPN). Patients were also required to be on a stable dosing regimen of antidiabetic medication, and have a hemoglobin A1c of not greater than 11% at screening, and a fasting plasma glucose of not greater than 310 mg/dL at screening. Patients who had previously not responded to treatment for DPN with gabapentin at doses greater than or equal to 1200 mg, patients who experienced dose-limiting adverse events that prevented titration of gabapentin to an effective dose, and patients who were hypersensitive to gabapentin were excluded from the study. Additional exclusion criteria, primarily focused on co-existing medical conditions, were also applied to patients. Baseline pain values for all eligible patients were determined during a one-week pretreatment period where the patients based their pain on the 11-point Lickert scale. Patients with a mean baseline score of at least a 4 on the 11-point scale together with the completion of at least 4 days of diary entries were eligible to participate in the study. All patients were required to undergo an appropriate washout for medications prescribed for pain associated with DPN prior to the Baseline period.

The 147 patients selected for the study were randomly assigned to treatment with 3000 mg of gastric retentive gabapentin GR dosed once daily following the evening meal (46 patients), or dosed twice daily with 1200 mg in the morning and 1800 mg in the evening (50 patients), against a placebo (51 patients). The course of the study was five weeks. Patients randomized to active treatment were gradually titrated over a two-week period to a total daily dose of 3000 mg, followed by an additional two-week period at the 3000 mg/day maintenance dose. All patients, regardless of treatment, took the same number of tablets of identical appearance each day to maintain the study blind; accordingly, patients assigned to placebo received no drug, but took the same number of tablets each day as those patients assigned to active treatments. A one-week blinded tapering period followed the four-week efficacy treatment period. End of study safety assessments were completed at the Week 5 visit.

The gastric retentive gabapentin GR dosage units prepared for administration to the patients were 300 mg and 600 mg white film coated, modified oval-shaped tablets with a total mass of 714 mg and 1020 mg, respectively. In addition to gabapentin, the tablets included the following inactive ingredients: polyethylene oxide, hypromellose (hydroxypropyl methylcellulose), magnesium stearate, binder, and coating. The placebo tablets were coated tablets comprised of only excipients, and were manufactured to have the same appearance as the active product.

The results of the study are shown in Tables 13-15. In all tables, patients who had both baseline and endpoint values were included in the data analysis. In accordance with standard statistical analyses, a lower p-value represents stronger evidence against the null hypothesis of no effect in the population being tested ($p=1.00$)

In Tables 13, 14 and 15 the "p values" (both overall and vs. placebo) are based on a Type III sum of squares statistical analysis; the LS (least square) mean and SEM (standard error of the mean) values for the Baseline are estimated from the ANOVA (ANalysis Of Variance) model that includes treatment, center and treatment by center interaction factor; and the LS mean and SEM values for the Endpoint and Change from Baseline to Endpoint are estimated from the ANCOVA (ANalysis of COVAriance) model that includes, treatment, center, treatment by center interaction factor, and baseline value as a covariate.

In Table 14, the "responders" are defined as patients with at least 50% reduction in BOCF (baseline observation carried forward) average daily pain score from Baseline; the "overall p-value" is based on a Cochran-Mantel-Haenszel test for the general association stratified by the baseline pain score category (less than 8 vs. at least 8); and the "p-value vs. placebo" is based on the Z test for the difference in proportions between the two groups (i.e., the treatment groups and the placebo group).

TABLE 13

ANALYSIS OF LOCF AVERAGE DAILY PAIN SCORE

| AVERAGE DAILY PAIN SCORE | TREATMENT GROUP | | | OVERALL TREATMENT p-value[1] |
|---|---|---|---|---|
| | GABAPENTIN GR (3000 mg PM) n = 46 | GABAPENTIN GR (3000 mg AM/PM) N = 50 | PLACEBO n = 51 | |
| Baseline | | | | |
| Mean (SD) | 6.71 (1.34) | 6.44 (1.51) | 6.74 (1.37) | 0.660 |
| LS Mean (SEM) | 6.79 (0.23) | 6.69 (0.23) | 6.97 (0.22) | |
| 95% CI | (6.33, 7.25) | (6.24, 7.14) | (6.53, 7.41) | |
| p-value (vs. placebo) [2] | 0.571 | 0.370 | | |
| LOCF Endpoint | | | | |
| Mean (SD) | 3.84 (1.83) | 4.48 (2.27) | 5.26 (1.93) | 0.002 |
| LS Mean (SEM) | 3.87 (0.29) | 4.65 (0.28) | 5.24 (0.28) | |
| 95% CI | (3.29, 4.44) | (4.10, 5.21) | (4.69, 5.80) | |
| Change from Baseline to LOCF Endpoint | | | | |
| Mean (SD) | −2.87 (1.97) | −1.96 (2.04) | −1.48 (1.94) | 0.002 |
| LS Mean (SEM) | −2.76 (0.29) | −1.98 (0.28) | −1.38 (0.28) | |
| 95% CI | (−3.34, −2.19) | (−2.53, −1.42) | (−1.94, −0.83) | |
| Gabapentin GR minus Placebo | | | | |
| LS Mean Δ (SEM) | −1.38 (0.38) | −0.59 (0.37) | N/A | |
| 95% CI for Δ | (−2.13, −0.63) | (−1.33, 0.14) | | |

TABLE 13-continued

ANALYSIS OF LOCF AVERAGE DAILY PAIN SCORE

| AVERAGE DAILY PAIN SCORE | GABAPENTIN GR (3000 mg PM) n = 46 | GABAPENTIN GR (3000 mg AM/PM) N = 50 | PLACEBO n = 51 | OVERALL TREATMENT p-value[1] |
|---|---|---|---|---|
| p-value (vs. placebo) [2] | <0.001 | 0.114 | | | n = sample size;
GR = gastric retentive;
LOCF = last observation carried forward;
LS least squares;
SEM = standard error of LS mean;
CI = confidence interval;
Δ = Difference;
N/A = not applicable
[1] The p-value (overall) for the overall comparison among all treatment groups is based on type III analysis
[2] The p-value (vs. Placebo) for the pairwise test of difference of the LS mean change from baseline between Gabapentin GR and placebo groups is based on the t-test of Type III analysis from the models described above.

TABLE 14

PROPORTION OF RESPONDERS AT ENDPOINT BASED ON BOCF

| AVERAGE DAILY PAIN SCORE | GR GABAPENTIN (3000 mg PM) n = 46 | GR GABAPENTIN (3000 mg AM/PM) n = 50 | PLACEBO n = 51 | OVERALL TREATMENT p-value |
|---|---|---|---|---|
| Responders at Endpoint | | | | |
| Yes | 16 (34.8%) | 13 (26.0%) | 4 (7.8%) | 0.005 |
| No | 30 (65.2%) | 37 (74.0%) | 47 (92.2%) | |
| Gabapentin GR minus Placebo | | | | |
| Difference in Yes Responders | 27.00% | 18.20% | | |
| 95% CI of DP | (11.39%, 42.61%) | (3.99%, 32.41%) | N/A | |
| p-value (vs. placebo) | 0.001 | 0.015 | | | n = sample size;
GR = Gastric Retentive;
DP = Difference in proportions;
CI = confidence interval
N/A = not applicable;
BOCF = Baseline Observation Carried Forward

TABLE 15

PERCENT CHANGE FROM BASELINE TO ENDPOINT IN BOCF AVERAGEDAILY SLEEP INTERFERENCE SCORE

| AVERAGE DAILY PAIN SCORE | GABAPENTIN GR (3000 mg PM) n = 46 | GABAPENTIN GR (3000 mg AM/PM) n = 50 | PLACEBO n = 51 | OVERALL TREATMENT p-value[1] |
|---|---|---|---|---|
| Baseline | | | | |
| Mean (SD) | 6.24 (1.81) | 5.61 (2.37) | 6.22 (1.94) | 0.421 |
| LS Mean (SEM) | 6.30 (0.35) | 5.79 (034) | 6.38 (0.34) | |
| 95% CI | (5.61, 7.00) | (5.11, 6.47) | (5.71, 7.04) | |
| p-value (vs. placebo) [2] | 0.879 | 0.225 | | |
| LOCF Endpoint | | | | |
| Mean (SD) | 3.16 (2.21) | 3.23 (2.73) | 4.41 (2.32) | 0.009 |
| LS Mean (SEM) | 2.98 (0.31) | 3.49 (0.30) | 5.23 (0.30) | |
| 95% CI | (2.36, 3.59) | (2.89, 4.08) | (3.64, 4.82) | |

TABLE 15-continued

PERCENT CHANGE FROM BASELINE TO ENDPOINT IN
BOCF AVERAGEDAILY SLEEP INTERFERENCE SCORE

TREATMENT GROUP

| AVERAGE DAILY PAIN SCORE | GABAPENTIN GR (3000 mg PM) n = 46 | GABAPENTIN GR (3000 mg AM/PM) n = 50 | PLACEBO n = 51 | OVERALL TREATMENT p-value[1] |
|---|---|---|---|---|
| Change from Baseline to LOCF Endpoint ||||| 
| Mean (SD) | −3.08 (2.06) | −2.39 (2.21) | −1.81 (2.25) | 0.009 |
| LS Mean (SEM) | −3.04 (0.31) | −2.53 (0.30) | −1.79 (0.30) | |
| 95% CI | (−3.65, −2.42) | (−3.13, −1.94) | (−2.38, −1.20) | |
| Gabapentin GR minus Placebo ||||| 
| LS Mean Δ (SEM) | −1.25 (0.41) | −0.74 (0.40) | N/A | |
| 95% CI for Δ | (−2.05, −0.45) | (−1.53, 0.05) | | |
| p-value (vs. placebo) [2] | 0.003 | 0.066 | | | n = sample size;
GR = gastric retentive;
LOCF = last observation carried forward;
LS = least squares;
SEM = standard error of LS mean;
CI = confidence interval;
N/A = not applicable
[1]The p-value (overall) for the overall comparison among all treatment groups is based on type III analysis from the models described above
[2] The p-value (vs. Placebo) for the pairwise test of difference of the LS mean change from baseline between Gabapentin GR and placebo groups is based on the t-test of Type III analysis from the models described above.

The Overall Treatment p-values in Table 13 show that the group as a whole experienced a statistically significant decrease in pain from Baseline to the end of efficacy based upon LOCF (Last Observation Carried Forward). While Table 13 shows a relatively large placebo effect, the p-value (vs. placebo) for the gabapentin treatment group for once-daily evening dosing indicates a statistically significant decrease in the pain experienced by the patients from Baseline to the end of efficacy period (see, p-values (vs. placebo) at Baseline and for GR Gabapentin minus Placebo). Between the two treatment groups, patients administered the twice-daily gastric retentive gabapentin showed less pain reduction than did the patients on the once-daily dosing regimen.

Table 14 shows that 34.6% of the patients following the once-daily dosing regimen and 26.0% of the patients following the twice-daily dosing regimen experienced a 50% reduction in pain from Baseline to the end of efficacy period (based on BOCF analysis), For both the once-daily dosing regimen and the twice-daily dosing regimen the difference in responders defined as those patients who experienced a 50% reduction in pain from Baseline to the end of efficacy period was statistically different from placebo.

Table 15 sets forth the change in Average Daily Sleep Interference Score from baseline to the end of the efficacy period. The data from Table 15 shows statistical differences from placebo in the change in sleep interference score from Baseline to the end of efficacy period for patients on the once-daily dosing regimen. For the twice-daily dosing regimen, the difference does not reach statistical significance.

Example 12

To study the rate and extent of absorption of the gastric retentive gabapentin (gabapentin GR) dosage forms of the present invention, a three-arm, randomized open-label, multiple dose, study was conducted on healthy non-smoking male and female subjects between the ages of 18 and 65.

The objective of the study was to compare the pharmacokinetics of gabapentin on Day 1 and on Day 8 (after 5 days of administration) for 2 different dosing regimes of gastric retentive gabapentin GR (Depomed Inc., Menlo Park, Calif.) administered under fed condition compared to three times daily dosing of the reference product, NEURONTIN® tablets.

Twenty-four nonsmoking male or female subjects between the ages of 18-65 years old were enrolled. Twenty-one subjects completed the study. The drug administration protocol was as follows:

TREATMENT GROUP A—after an overnight fast of at least 10 hours, one 600 mg gastric retentive gabapentin GR tablet was administered with 240 mL of a water 20 minutes after the start of a standardized meal at 8:00 a.m. and the second and third 600 mg gastric retentive gabapentin GR tablets (2 tablets) were administered with 240 mL of water 20 minutes after the start of a standardized meal at 8:00 p.m. (20:00). The total treatment dose was 1800 mg. The Day 1 dosing was followed by two days without drug administration. Then a steady-state period was initiated in which this treatment regimen was repeated for five consecutive days (Days 4-8).

TREATMENT GROUP B—three 600 mg gastric retentive gabapentin GR tablets were administered with 240 mL of water 20 minutes after the start of a standardized meal at 8:00 p.m. (20:00). The total treatment dose was 1800 mg. The Day 11 dosing was followed by two days without drug administration. Then a steady-state period was initiated in which this treatment regimen was repeated for five consecutive days (Days 4-8).

TREATMENT GROUP C—after an overnight fast of at least 10 hours, one NEURONTIN® tablet containing 600 mg gabapentin was administered with 240 mL of water at 8:00 a.m., 2:00 p.m. (14:00) and 8:00 p.m. (20:00). All doses were administered 20 minutes after the start of standardized meals. The total treatment dose was 1800 mg. The Day 1 dosing was followed by two days without drug administration. Then a steady-state period was initiated in which this treatment regimen was repeated for five consecutive days (Days 4-8).

The length of the study was three periods in which treatment was administered on day 1 and days 4-8 separated by at least one-week washout period between treatments. Blood samples were drawn in each three-day-period up to 36.0 hours post-dose.

A summary of some of the important steady-state pharmacokinetic parameters are shown in Table 16 below. As shown in table 16, at steady-state the gabapentin GR dosed twice per day (600 mg in the morning, 1200 mg in the evening) shows similar bioavailability to NEURONTIN® immediate release tablets dosed three times per day (600-mg dose at 8:00 a.m., 2:00 p.m. and 8:00 p.m.) as evidenced by the ratio of mean $AUC^{0-inf}$ of 102%. Also note that the Gabapentin GR maximum plasma concentration is about 19% lower and the minimum plasma concentration is about 18% higher than the maximum and minimum concentrations, respectively, for the TID dosing of the NEURONTIN® immediate release tablets. The data is an illustration that this embodiment of the present invention has provided improved convenience of dosing (twice per day versus three times per day) with a smoother plasma profile as evidenced by the lower maximum and higher minimum plasma concentrations without any loss of bioavailability.

Furthermore, the once daily dosing of this embodiment of the present invention also compares favorably with the TID dosing of the of the NEURONTIN® immediate release tablets. Although the minimum concentration is about 50% lower, the maximum plasma concentration is only about 16% higher than that observed for NEURONTIN® immediate release tablets. There is a modest loss in bioavailability (ratio of the means of the bioavailability for gabapentin GR dosed once daily to the NEURONTIN® immediate release tablet is 93%), but a significant increase in dosing convenience with a regimen of three times daily dosing compared to once daily dosing after the evening meal,

TABLE 16

COMPARISON OF DOSING REGIMENS BASED ON DAY 8 DOSING

| Parameter | 90% C.I. | Ratio of Means | Intra-Subject CV |
|---|---|---|---|
| Treatment A versus Treatment B | | | |
| $AUC_{0-24}$ | 102% to 117% | 110% | 13% |
| $C_{max}$ | 66% to 75% | 70% | 12% |
| $C_{min}$ | 205% to 248% | 225% | 18% |
| Treatment A versus Treatment C | | | |
| $AUC_{0-24}$ | 95% to 109% | 102% | 13% |
| $C_{max}$ | 76% to 86% | 81% | 12% |
| $C_{min}$ | 107% to 130% | 118% | 18% |
| Treatment B versus Treatment C | | | |
| $AUC_{0-24}$ | 87% to 100% | 93% | 13% |
| $C_{max}$ | 109% to 123% | 116% | 12% |
| $C_{min}$ | 48% to 56% | 52% | 18% |

We claim:

1. A method of treating a symptom associated with menopause in a subject experiencing said symptom, comprising:
    administering to the subject a daily dose of 100 mg gabapentin in a gastric retentive dosage form comprising a hydrophilic polymer that upon ingestion swells to a size sufficient to achieve retention of the dosage form in the stomach in a fed mode for a period of at least about five hours,
    wherein the daily dose is administered as a 600 mg dose with a morning meal and a 1200 mg dose with an evening meal,
    and wherein the subject is experiencing hot flashes.

2. The method of claim 1, wherein the subject is a menopausal female.

3. The method of claim 1, wherein the hydrophilic polymer comprises polyethylene oxide.

4. The method of claim 1, wherein the hydrophilic polymer comprises hydroxypropylmethylcellulose.

5. A method for treating hot flash in a subject comprising:
    administering to the subject in need thereof gabapentin in a gastric retentive dosage form comprising a hydrophilic polymer that upon ingestion swells to a size sufficient to achieve retention of the dosage form in the stomach in a fed mode for a period of at least about five hours,
    wherein said daily dose is administered as a 600 mg dose with a morning meal and a 1200 mg dose with an evening meal.

6. The method of claim 5, wherein the subject is a human.

7. The method of claim 6, wherein the human is a female.

8. The method of claim 7, wherein the female is a menopausal female.

9. The method of claim 6, wherein the human is a male.

10. The method of claim 5, wherein the subject has undergone or is undergoing chemotherapy.

11. The method of claim 5, wherein the hydrophilic polymer comprises polyethylene oxide.

12. The method of claim 5, wherein the hydrophilic polymer comprises hydroxypropylmethylcellulose.

* * * * *

UNITED STATES PATENT AND TRADEMARK OFFICE
CERTIFICATE OF CORRECTION

PATENT NO.      : 8,592,481 B2  
APPLICATION NO. : 13/707961  
DATED           : November 26, 2013  
INVENTOR(S)     : Berner et al.

Page 1 of 1

It is certified that error appears in the above-identified patent and that said Letters Patent is hereby corrected as shown below:

In The Claims

Claim 1, Column 50, line 15: change "a daily dose of 100 mg" to --a daily dose of 1800 mg--

Signed and Sealed this
Nineteenth Day of April, 2016

Michelle K. Lee
*Director of the United States Patent and Trademark Office*